US009585708B2

(12) United States Patent
Asirvatham et al.

(10) Patent No.: US 9,585,708 B2
(45) Date of Patent: *Mar. 7, 2017

(54) CONTROLLING COAGULUM FORMATION

(71) Applicant: Mayo Foundation for Medical Education and Research, Rochester, MN (US)

(72) Inventors: Samuel J. Asirvatham, Rochester, MN (US); Arshad Jahangir, Rochester, MN (US); Bernard B. C. Lim, Rochester, MN (US); Kalpathi L. Venkatachalam, Jacksonville Beach, FL (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/014,991

(22) Filed: Feb. 3, 2016

(65) Prior Publication Data
US 2016/0151105 A1    Jun. 2, 2016

Related U.S. Application Data

(60) Continuation of application No. 14/330,671, filed on Jul. 14, 2014, now Pat. No. 9,271,786, which is a
(Continued)

(51) Int. Cl.
*A61B 18/10* (2006.01)
*A61B 18/12* (2006.01)
(Continued)

(52) U.S. Cl.
CPC ............ *A61B 18/10* (2013.01); *A61B 18/082* (2013.01); *A61B 18/1206* (2013.01);
(Continued)

(58) Field of Classification Search
CPC ............ A61B 18/1492; A61B 18/1233; A61B 18/1206; A61B 2018/00446;
(Continued)

(56) References Cited

U.S. PATENT DOCUMENTS 3,491,756 A    1/1970    Bentov
4,686,987 A    8/1987    Salo et al.
(Continued)

FOREIGN PATENT DOCUMENTS

WO    WO 2007/121281    10/2007
WO    WO 2008/121814    10/2008

OTHER PUBLICATIONS

Aashiish Agnihotri and Christopher A. Siedlecki Time-Dependent Conformational Changes in Fibrinogen Measured by Atomic Force Microscopy Langmuir 2004, 20, 8846-8852.
(Continued)

*Primary Examiner* — Manuel Mendez
(74) *Attorney, Agent, or Firm* — Fish & Richardson P.C.

(57) ABSTRACT

Some embodiments of a medical instrument can be configured to reduce the formation of coagulum by delivering a negative charge bias to conductive surfaces that interface with blood or bodily tissue during a medical procedure. The application of the negative charge at the instrument-blood interface can reduce the fibrinogen deposition and the formation of coagulum because fibrinogen molecules in general are negatively charged at neutral pH levels. In addition, some embodiments of the instrument may be configured to irrigate the instrument-blood interface with RGD/ClfA peptides, a bicarbonate solution (or other high pH solution), or both to further repel the fibrinogen and thereby inhibit the formation of coagulum. Accordingly, some embodiments of the medical instrument can substantially reduce the risks of thromboembolism during particular medical procedures.

20 Claims, 16 Drawing Sheets

Related U.S. Application Data continuation of application No. 13/371,539, filed on Feb. 13, 2012, now Pat. No. 8,790,338, which is a division of application No. 12/389,991, filed on Feb. 2, 2009, now Pat. No. 8,409,192, which is a continuation-in-part of application No. PCT/US2007/076318, filed on Aug. 20, 2007.

(60) Provisional application No. 60/838,983, filed on Aug. 21, 2006.

(51) Int. Cl.
| | |
|---|---|
| A61B 18/14 | (2006.01) |
| A61B 18/08 | (2006.01) |
| A61B 17/00 | (2006.01) |
| A61B 18/00 | (2006.01) |
| A61M 25/00 | (2006.01) |
| A61N 1/20 | (2006.01) |

(52) U.S. Cl.
CPC ...... *A61B 18/1233* (2013.01); *A61B 18/1492* (2013.01); *A61B 2017/00575* (2013.01); *A61B 2018/0041* (2013.01); *A61B 2018/0075* (2013.01); *A61B 2018/00351* (2013.01); *A61B 2018/00446* (2013.01); *A61B 2018/00577* (2013.01); *A61B 2018/00642* (2013.01); *A61B 2018/00702* (2013.01); *A61B 2018/00791* (2013.01); *A61B 2018/00875* (2013.01); *A61B 2218/002* (2013.01); *A61M 25/0071* (2013.01); *A61N 1/205* (2013.01)

(58) Field of Classification Search
CPC .. A61B 2018/00577; A61B 2018/0041; A61B 2018/00875; A61B 2218/002; A61B 2018/00702; A61B 2018/00791; A61B 2017/00575; A61B 2018/00642; A61B 2018/0075; A61B 2018/00351; A61B 18/10; A61B 18/082; A61M 25/0071; A61N 1/205
USPC ........... 604/22, 65–67; 606/41, 33, 14, 1, 20
See application file for complete search history.

(56) References Cited

U.S. PATENT DOCUMENTS

| | | | |
|---|---|---|---|
| 5,496,312 | A | 3/1996 | Kilcek |
| 5,500,012 | A | 3/1996 | Brucker et al. |
| 5,855,578 | A | 1/1999 | Guglielmi et al. |
| 5,913,856 | A | 6/1999 | Chia et al. |
| 6,074,387 | A | 6/2000 | Heim et al. |
| 6,492,332 | B1 | 12/2002 | Demopulos et al. |
| 6,887,270 | B2 | 5/2005 | Miller et al. |
| 6,918,869 | B2 | 7/2005 | Shaw et al. |
| 7,494,488 | B2 | 2/2009 | Weber |
| 8,409,192 | B2 * | 4/2013 | Asirvatham ....... A61B 18/1206 606/41 |
| 8,790,338 | B2 * | 7/2014 | Asirvatham ....... A61B 18/1206 606/41 |
| 9,271,786 | B2 * | 3/2016 | Asirvatham ....... A61B 18/1206 |
| 2002/0120264 | A1 | 8/2002 | Crowley et al. |
| 2003/0069601 | A1 | 4/2003 | Nowakowski et al. |
| 2003/0078644 | A1 | 4/2003 | Phan |
| 2003/0138499 | A1 | 7/2003 | Shah et al. |
| 2003/0199864 | A1 | 10/2003 | Eick |
| 2004/0006337 | A1 | 1/2004 | Nasab et al. |
| 2004/0186465 | A1 | 9/2004 | Francischelli et al. |

OTHER PUBLICATIONS

B.C.B Lim, Atomic Force Microscopy of Fibrinogen on Different Surface Materials: Implications for Implantation Biophysical Journal 2005; vol. 88(1):Part 2 of 2: 557a.

Baiyan Xie MD, Francis D. Murgatroyd MRCP, Spencer C. Heald MD, A. John Camm Md, Edward Rowland MD and David E. Ward MD, "Late Follow-Up of Catheter Ablation of Atrial Flutter using Low-Energy Direct Current," *American J. Cariology*, Nov. 1, 1994, 7 pages.

Cross-linking of fibrin by Factor XIII and its Effect on Fibrin Structure/Function B.C.B. Lim, R.A.S. Ariens, S.D. Connell, D.A. Smith, J.W. Weisel, P.J. Grant Circulation 2003; vol. 108(17):IV 30 (Suppl).

Deivanayagam CC et al. A novel variant of the immunoglobulin fold in surface adhesions of Staphylococcal aureus: crystal structure of the fibrinogen binding MSCRAMM, clumping factor A. EMBO 2002;21:6660-6672.

EPO Communication pursuant to Article 94(3) EPC for Application No. 07841112.1, dated Mar. 26, 2012,5 pages.

Fatah, K , Hamsten, A., Blomback, B. and Blomback, M. (1992) Fibrin gel network characteristics and coronary heart disease: relations to plasma fibrinogen concentration, acute phase protein, serum lipoproteins and coronary atherosclerosis. *Thromb Haemost* 68, 130-135.

Fatah, K , Silveira, A., Tornvall, P., Karpe, F., Blomback, M. and Hamsten, A. (1996b) Proneness to formation of tight and rigid fibrin gel structures in men with myocardial infarction at a young age. *Thromb Haemost* 76, 535-540.

Hawiger JS et al. Identification of a region of human fibrinogen interacting with staphylococcal clumping factor. Biochemistry 1982;21:1407-13.

Hui-shan Tung, "A bone sialoprotein-binding protein from *Staphylococcus aureus:* a member of the staphylococcal Sdr family" Biochem. J. vol. 345, pp. 611-619, 2000.

J. Hemmerle, S.M. Altmann, M. Maaloum, J.K. Horber, L. Heinrich, J.C. Voegel, P. Schaaf. Direct observation of the anchoring process during the adsorption of fibrinogen on a solid surface by force-spectroscopy mode atomic force microscopy. Proc. Natl. Acad. Sci. USA 96(Jun. 8, 1999):6705-6710.

James Galit et al. "Human Fibroblasts Bind Directly to Fibrinogen at RGD Sites through Integrinavb3" Experimental Cell Research vol. 232, pp. 118-126, 1997.

Johanna Armstrong. Interfacial adsorption of fibrinogen and its inhibition by RGD peptide: a combined physical study, J. Phys.: Condens. Matter 16 2004 S2483-S2491.

Julie M. Demolin et al , Soft Thrombus Formation in Radiofrequency Catheter Ablation Journal of Pacing and Clinical Electrophysiology, vol. 25, No. 8, Aug. 2002.

Karlis Adamsons, Jr. et al Influence of temperature on blood pH of the human adult and newborn. Journal Appl Physiol Sep. 1964;19:897-900.

Lemery R, Talajic M, Roy D, Coutu B, Lavoie L, Lavallée E, Cartier R., "Success, safety, and late electrophysiological outcome of low-energy direct-current ablation in patients with the Wolff-Parkinson-White syndrome " *Circulation*, Mar. 1992:85(3):957-62.

Lemery R, Talajic M, Roy D, Lavoie L, Coutu B, Hii JT, Radzik D, Lavallee E, Cartier R., "Results of a comparative study of low energy direct current with radiofrequency ablation in patients with the Wolff-Parkinson-White syndrome", *Br. Heart J.*, Dec. 1993;70(6):580-4.

Leo Vroman, Ann L. Adams Findings with the Recording Ellipsometer Suggesting Rapid Exchange of Specific Plasma Proteins at Liquid-Solid Interfaces. Surface Sci. 16(1969):438-448.

Leo Vroman, Ann L. Adams Identification of Adsorbed Protein Films by Exposure to Antisera and Water Vapor. J. Biomed. Mater. Res. 3(1969):669-671.

Leo Vroman, Ann L. Adams Identification of Rapid Changes at Plasma-Solid Interfaces. J. Biomed. Mater. Res. 3(1969):43-67.

Liu CZ et al. ClfA221-550, a fibrinogen binding segment of *Staphylococcus aureus* clumping factor A, disrupts fibrinogen function. Thromb Haemost 2005;94:286-94.

McDevitt D et al. Characterization of the interaction between the *Staphylococcus aureus* clumping factor (ClfA) and fibrinogen. Eur J Biochem 1997;247:416-424.

(56) References Cited

OTHER PUBLICATIONS

McDevitt D et al. Molecular characterization of the clumping factor (fibrinogen receptor) of *Staphylococcus aureus*. Molecular Microbiology 1994;11:237-248.
Metcalfe MS, et al. "The safety and efficacy of radiofrequency and electrolytic ablation created adjacent to large hepatic veins in a porcine model" EJSO, 33, (2007) 662-667.
P.S. Sit, R.E. Marchant. Surface-dependent conformations of human fibrinogen observed by atomic force microscopy under aqueous conditions. Thromb. Haemost. 82(Sep. 1999):1053-1060.
R.E. Baier, R.C. Dutton, Initial Events in Interactions of Blood with a Foreign Surface. J. Biomed. Mater. Res. 3(1969):191-206.
Roger Wigren et al., Structure of adsorbed fibrinogen obtained by scanning force microscopy, FEBS Letters 1991 280(2) 225-8.
Seung-Yong Jung, Soon-Mi Lim, Fernando Albertorio, Gibum Kim, Marc C. Gurau, Richard D. Yang, Matthew A. Holden, and Paul S. Cremer The Vroman Effect: A Molecular Level Description of Fibrinogen Displacement J. Am. Chem. Soc. 9 vol. 125, No. 42, 2003.
Ukigusa et al., "[Prolongation of ischemic tolerance time of donor livers by alkaline preservation solutions]," Res Exp Med (Berl). 184(2):103-113, 1984 [article in German] English abstract only, 1 page.
Office Action in European Application No. 07841112.1 dated Nov. 29, 2013, 5 pages.

\* cited by examiner

Ablation - No Charge

Ablation - Negative Charge

No Charge - No Ablation

Negative Charge - No Ablation

A - No Charge

C - Negative Charge

B - Positive Charge

D - No Charge

CONTROLLING COAGULUM FORMATION

CROSS REFERENCES TO RELATED APPLICATION

This application is a continuation of U.S. application Ser. No. 14/330,671, filed Jul. 14, 2014 and entitled "Controlling Coagulum Formation" (now U.S. Pat. No. 9,271,786), which is a continuation of U.S. application Ser. No. 13/371,539 filed Feb. 13, 2012 and entitled "Controlling Coagulum Formation" (now U.S. Pat. No. 8,790,338), which is a divisional of U.S. application Ser. No. 12/389,991 filed on Feb. 20, 2009 and entitled "Controlling Coagulum Formation" (now U.S. Pat. No. 8,409,192), which is a continuation-in-part of PCT/US2007/076318 filed on Aug. 20, 2007 and entitled "Controlling Coagulum Formation" (WO2008/024714), which claims the benefit of U.S. Provisional Application Ser. No. 60/838,983 filed on Aug. 21, 2006 by Samuel J. Asirvatham et al, the disclosures of which are incorporated herein by reference in their entirety.

TECHNICAL FIELD

This document relates to techniques for reducing the likelihood of coagulum formation during medical treatments inside the body, for example, by reducing direct fibrinogen binding and fibrinogen denaturation that can occur during ablation therapy.

BACKGROUND

A number of medical treatments include the insertion of catheters, implants, or other devices into the patient's blood stream. Such contact with the blood may cause thrombus formation and subsequent embolization. Various therapies may be used to limit these consequences, including the infusion of heparin or other anticoagulants into the bloodstream.

In one example, radiofrequency (RF) ablation can be used to treat various arrhythmias including atrial fibrillation, ventricular tachycardia and supraventricular tachycardia. RF ablation can be performed percutaneously, a procedure in which a catheter is introduced into the patient through an artery or vein and directed to the atrium or ventricle of the heart to perform one or more procedures. In such circumstances, the RF ablation procedure is used to destroy the tissue causing the arrhythmia in an attempt to remove the electrical signal irregularities or create a conductive tissue block to restore normal heart rhythm. Successful ablation of the conductive tissue at the arrhythmia initiation site may terminate the arrhythmia or reduce the frequency of the arrhythmia to acceptable levels. When multiple applications of energy are required to treat a clinical arrhythmia (e.g., atrial fibrillation or ventricular tachycardia), thrombus formation and subsequent embolization giving rise to stroke or other embolic sequelae become an important limiting factor. In an effort to limit such complications, therapy such as intravenous anticoagulation can be employed (e.g., infusion of heparin or other anticoagulants to the blood).

Although heparinization can reduce the chance of thrombus formation associated with denuded endothelium, stroke and other thromboembolic events may occur despite adequate heparinization. For example, during RF ablation clotted components (e.g., coagulum) of blood may form along the tip portion of the ablation catheter and the ablated tissue, increasing the effective impedance between the ablation catheter and tissue and also increasing the risk of embolization of the coagulum. One reason is that RF ablation is associated with a direct conversion of fibrinogen to fibrin and subsequently to char. This fibrin and char can potentially lead to embolization even in the absence of thrombin. Accordingly, the coagulum can be formed during RF ablation even if heparin is adequately supplied to reduce thrombin in the blood.

SUMMARY

Some embodiments of a medical instrument can be configured to reduce the formation of coagulum by delivering a negative charge bias to conductive surfaces that interface with blood or bodily tissue during a medical procedure. For example, particular cardiac treatment devices (e.g., RF ablation catheters, heat cautery instruments, and others), brain treatment devices (e.g., deep-brain stimulation electrodes, cortical mapping electrodes, and others), and blood sensor devices (e.g., glucose sensors and others) may include electrode surfaces or other conductive surfaces that interface with the blood during operation in a manner that may permit the fibrinogen in the blood to deposit and form coagulum. However, as described herein, the application of the negative charge at the instrument-blood interface can reduce the fibrinogen deposition and the formation of coagulum because fibrinogen molecules in general are negatively charged at neutral pH levels. In addition, some embodiments of the instrument may be configured to irrigate the instrument-blood interface with RGD/ClfA peptides, a bicarbonate solution (or other high pH solution), or both to further repel the fibrinogen and thereby inhibit the formation of coagulum. Accordingly, some embodiments of the medical instrument can substantially reduce the risks of thromboembolism during particular medical procedures.

In particular embodiments, a catheter device may be configured to reduce the formation of coagulum during medical procedures, such as an RF ablation procedure. For example, the catheter device may reduce the likelihood of fibrinogen bindings along the distal tip portion of the catheter body. Such a device may be employed to perform mapping procedures (e.g., detect electrograms) in addition to the RF ablation procedures.

As described herein, one such technique for reducing the formation of coagulum along the distal tip portion of the catheter device is to apply a negative electrical charge on the catheter body (e.g., along the electrode surfaces carried by the tip portion or along the entire outer surface of the tip portion or the whole catheter body) to repel fibrinogen from the electrode surfaces along the distal tip portion or along the catheter body. As such, the devices described herein may apply a negative charge along the distal tip portion of the catheter body so as to reduce the likelihood of fibrinogen binding and subsequent coagulum formation.

Another technique described herein is to provide open irrigation of a relatively high pH solution from output ports along the distal tip portion of the catheter device. It is believed that fibrinogen at lower pH levels will bind more tightly to electrode surfaces. By releasing a fluid from the catheter device that has a pH level higher that typical pH values for blood, the likelihood of fibrinogen binding may be reduced. For example, a bicarbonate solution having a higher pH level that blood can inhibit fibrinogen from tissue binding. In some circumstances, the high pH solution may also include RGD peptides of the fibrinogen molecules. The arginine lysine aspartame peptide sequence of fibrinogen is believed to be a cell recognition site for various adhesive proteins present in the extra cellular matrix and blood. For example, a peptide sequence (amino-acid residues 221-550) corresponding to Clumping Factor A (ClfA) of *Staphylococcus Aureus* can bind to the fibrinogen gamma chain C-terminus, thereby blocking fibrinogen from binding to electrode surfaces.

It should be understood from the description herein that these concepts can be applied to other catheter devices or implantable devices that come into contact with blood so as to reduce the formation of coagulum. For example, an angiographic catheter device may be constructed with a distal tip surface that can be negatively charged during use. Such a negative charge on the angiographic catheter tip portion may reduce the likelihood of clot formation during angiography and may reduce the usage of heparin or other anticoagulant drugs during the procedure. In a second example, a vascular sheath device used to deliver intravenous medications into the central venous system could also have a conductive coating, with very small sources of power delivering a negative charge on a continuous or intermittent basis. In a third example, a hemodialysis system may incorporate an electrically charged system that applies a negative charge to some or all of the catheters, tubes, and reservoirs of the dialysis machine pumps that contact the blood so as to reduce the need for heparin and reduce thrombosis. In a fourth example, a power control system can deliver a negative charge to a portion of a cardiac instrument that applies RF energy or heat energy during a cardiac procedure, such as a wire, mesh, tube, stent, blade, or other elements. For instance, the negative charge can be delivered to the RF ablation elements that are used to close or otherwise repair a patent foramen ovale (PFO) or delivered to RF heat cautery or cutting elements that are used for percutaneous valve removal or repair. Such a negative charge on a conductive portion of the cardiac instrument may reduce the likelihood of clot formation during the cardiac procedure and may reduce the usage of heparin or other anticoagulant drugs during the procedure. In a fifth example, a power control system can deliver a negative charge to a conductive surface of an implantable glucose sensor (e.g., for treatment of diabetics) so as to inhibit the formation of coagulum on the sensor that would otherwise reduce the sensor accuracy and service life. In a sixth example, brain treatment instrumentation (e.g., deep-brain stimulation electrodes, cortical mapping electrodes, sensing electrodes for detection of epileptic events), peripheral nerve stimulators to treat pain, and others) may incorporate a power control system that applies a negative charge to indwelling neural electrodes or the like so as to inhibit the formation of coagulum.

Finally, it should be understood from the description herein that the reverse approach (e.g., positively charging a surface to induce rapid clot formation) may also be employed on any number of medical devices. For example, as an alternative to alcohol ablation of the septum in hypertrophic cardiomyopathy (where one does not have total control of the alcohol flow), a thin wire device could be placed in the required artery to be ablated and charged positively after correct placement to induce rapid clot formation, with consequent interruption of blood flow. In another example, as a means of anchoring unstable catheters or wires (e.g., a pacemaker lead) immediately after placement, a positive charge on the delivery catheter surface or lead surface could be used to induce clot and thereby adhere the catheter to the vessel wall temporarily while fibrosis is taking place, reducing the likelihood of lead dislodgement. In a further example, superficial bleeding could be reduced by using conductive adhesive patches that could be positively charged to enhance clot formation and hemostasis.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION OF ILLUSTRATIVE EMBODIMENTS

Some embodiments of a medical instrument can be configured to provide a negative charge to conductive surfaces that interface with blood or bodily tissue during a medical procedure, thereby reducing the formation of coagulum at the internal treatment site. For example, cardiac treatment devices (refer, for example, to the ablation catheter depicted in FIGS. 1-3), blood sensor devices (refer, for example, to the blood glucose sensor depicted in FIG. 15), and brain treatment devices (refer, for example, to the deep-brain stimulation electrode depicted in FIG. 16) may include electrode surfaces or other conductive surfaces that interface with the blood during operation in a manner that may permit the fibrinogen in the blood to deposit and form coagulum. However, as described herein, the application of the negative charge at the instrument-blood interface can reduce fibrinogen binding and the formation of coagulum. A number of illustrative examples are described in more detail below.

Figure 1:
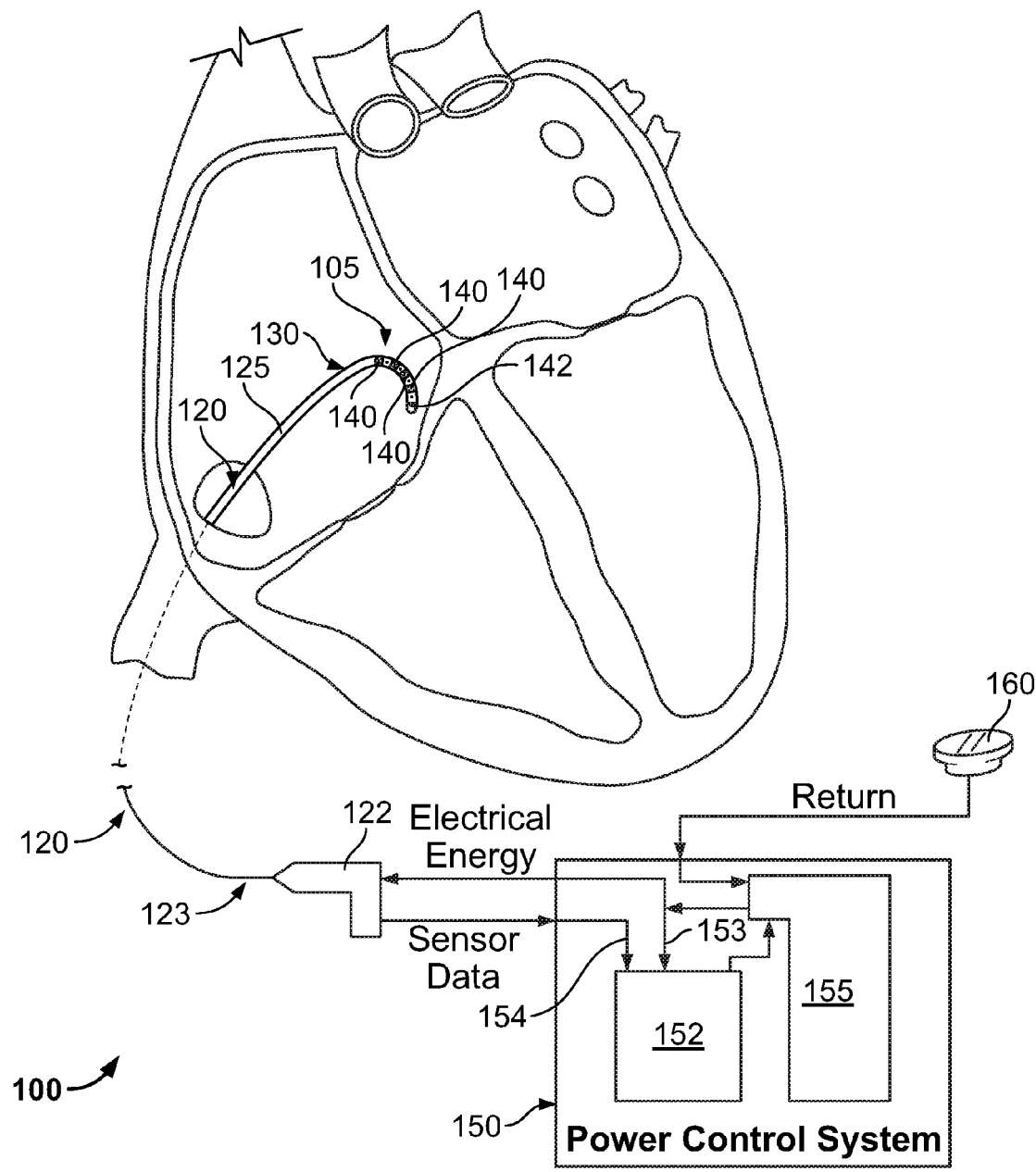
FIG. 1 is a diagram of a system for use in ablation therapy, in accordance with some embodiments.

Referring to FIG. 1, a system 100 for use in ablation therapy of a biological site, such as ablation of heart tissue 105, includes an ablation catheter device 120 and a power control system 150. The ablation catheter device 120 may include a handle 122 that joins with a proximal portion 123 of a steerable elongated shaft 125 (e.g., having one or more steering cables or a shape memory device, or the like). The elongate shaft 125 may also include a distal tip portion 130 that carries one or more electrodes 140 and 142 and that is capable of being directed to the targeted site via delivery through the patient's arterial or venous system.

In this embodiment, the ablation catheter device 120 is used to deliver RF ablation energy to the targeted tissue site so as to ablate or otherwise destroy the tissue proximate to the electrodes 140 and 142. For example, the ablation catheter device 120 can be used to destroy the heart tissue causing the arrhythmia in an attempt to remove the electrical signal irregularities or create a conductive tissue block to restore normal heart rhythm. Such an RF ablation technique can be used to treat various arrhythmias including atrial fibrillation, ventricular tachycardia and supraventricular tachycardia. As described in more detail below, the catheter device 120 can be used to reduce the likelihood of the formation of coagulum during RF ablation and thereby reduce the risk of embolization.

As shown in FIG. 1, the power control system 150 may include a power generator 155, that may have any number of output channels through which it provides electrical energy to the catheter device 120. The operation of the power generator 155 is controlled by a controller 152 which outputs control signals to the power generator 155. The controller 152 can monitor the electrical energy provided by the power generator 155 along a power monitor line 153. The controller 152 may also receive sensor data signals from the catheter device 120 along a sensor data line 154. For example, the catheter device may include one or more temperature sensors (e.g., thermocouples or the like) along the distal tip portion 130 so that temperature data signals are returned to the controller 152 via the sensor data line 154. In these circumstances, the controller 30 can adjust the operation of the power generator 155 based on the temperature sensed at the distal tip portion 130 of the catheter device. The power control system 150 may also be connected with a return electrode 160. The return electrode 160 can be connected to the power generator 155 and generally provides a return path for the ablation energy delivered to the targeted site 105 through the catheter device 120. For example, the return electrode 160 may comprise a patch electrode adhered to the patient's skin (e.g., on the patient's back) so as to serve as the opposite pole for the electrodes 140 and 142 disposed inside the patient's body along the distal tip portion 130.

The power control system 150 may be configured to deliver a negative charge to the distal tip portion 130 of the catheter device 120 (and, in some circumstances, a positive charge bias on the return electrode 160). Fibrinogen is a negatively charged molecule (refer to FIG. 4). Thus, the application of the negative charge at the ablation surface can reduce the fibrinogen deposition at the site. Such a negative charge can be accomplished in a number of ways. For example, the normal output stage of an RF ablation generator is transformer-coupled with series-and-parallel resonant (tank) circuits on the output to produce a sinusoidal waveform. The output is a 400-600 KHz sine wave with no DC offset, and thus the electrical charge is neutral for each cycle. The embodiments of the power generator 155 (FIG. 1) may include circuitry to add a relatively small DC offset to the sinusoidal waveform so that a negative charge bias is delivered to the electrodes 140 and 142 of the catheter device 120. Such circuitry may include a bridge rectifier, a separate DC power source, or other electronic circuits to delivery the DC offset to the waveform that is output from the RF ablation generator circuitry. Accordingly, a small DC voltage could be added to the AC output in series with a current-limiting resistor to produce a composite waveform (e.g. 50 Vrms riding on top of a 0.2V DC voltage). It should be understood from the description herein that the power generator 155 or another portion of the power control system 150 can be configured so that the correct polarity is selected to maintain a negative charge at the interface.

Such a relatively small DC voltage applied to the distal tip portion 130 of the ablation catheter device 120 can provide a continuous source of current (e.g., a negative charge). Accordingly, the electrical current delivered to the targeted tissue 105 during the ablation procedure may comprise a composite waveform (e.g., 600 milliAmp rms riding on top of a 50-100 microAmp continuous current). The continuous source of current may be sufficiently below the stimulation threshold for the muscle tissue (e.g., the myocardial tissue in the heart wall), thereby avoiding electrical stimulation of targeted tissue. This low-level electric current is converted to an ionic current at the electrode-tissue interface. As such, the negative charge may also be deposited on the targeted tissue surface, thereby further reducing the likelihood of fibrinogen binding along the targeted tissue surface.

Still referring to FIG. 1, the power control system 150 may comprise a single module that contains all components of the controller 152 and the power generator 155. In other embodiments, the power control system 150 may comprise a number of modules that are connectable to one another (as described, for example, in connection with FIGS. 10-11) to provide the previously described electrical output to the catheter device 120. For example, the power generator 150 may comprise one or more components (e.g., RF ablation generator, DC offset generator, etc.) that are individually or collectively connectable with the controller 152 that comprises at least one microprocessor-based controller circuit. One or more of these components may include a display screen or another user interface device so that a surgeon or other user can make adjustments to the electrical output and control parameters. The output of the power control system (e.g., sensor output and electrical signals from the patient) may also be connected to other components (e.g., mapping and display systems) to provide the operator with information from the tissue interface being interrogated.

Figure 2:
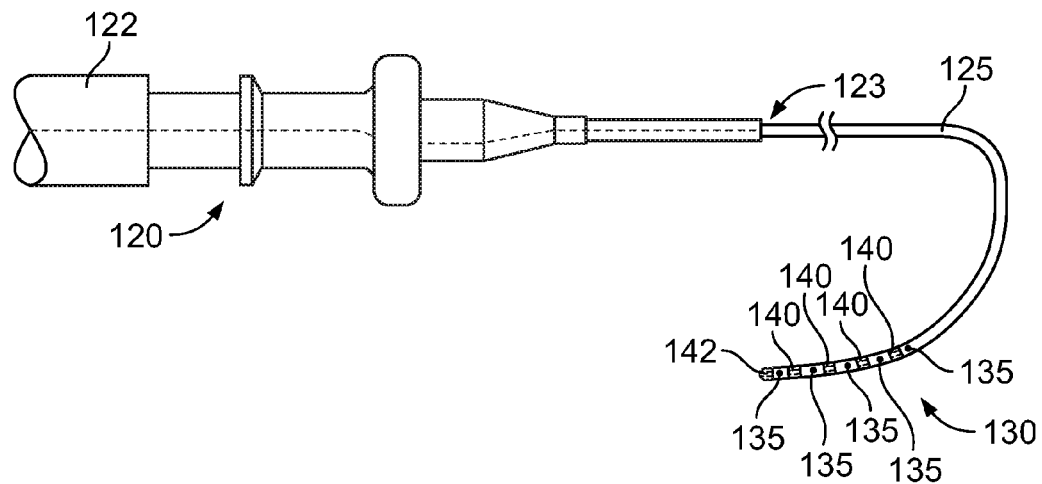
FIG. 2 is a perspective view of a catheter device of the system shown in FIG. 1.
Figure 3:
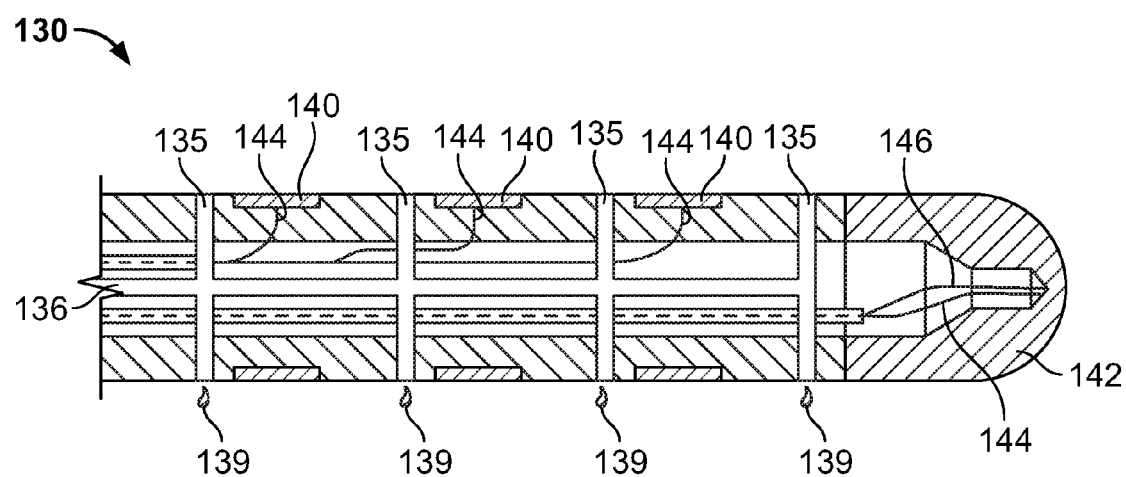
FIG. 3 is a partial cross-sectional view of the catheter device of FIG. 3.

Referring now to FIGS. 2-3, the distal tip portion 130 of the catheter device 120 includes a set of electrodes 140 and 142 arranged in a substantially linear array. The electrodes in this embodiments comprise four band electrodes 140 and one tip electrode 142. In this illustration, five electrodes are depicted in FIG. 2, but it should be understood that one or more electrodes can be provided along the distal tip portion 130 of the catheter device 120. The width of the electrodes may vary depending upon the diameter of the elongate body 125, the targeted tissue site 105, and other factors. For example, the electrodes 140 and 142 have a width of about 3-8 mm. It should be understood that the arrangement of the band electrodes 40 is not limited to a linear array and may take the form of other patterns such as circular and curvilinear arrays. The band electrodes 140 and tip electrode 142 can be formed of a material having a significantly higher thermal conductivity than that of the biological tissue to be ablated. Possible materials include gold, silver, chromium, aluminum, molybdenum, tungsten, nickel, platinum, and platinum/iridium alloys.

As shown in FIG. 3, each of the electrodes 140 and 142 may be electrically connected to the power control system 150 (FIG. 1) via electrical lines 144. The electrical lines 144 may pass through one or more lumens of the elongate catheter body 125. In some embodiments, each of the electrical lines 144 may be separate and may individually connect to the power control system 150. Alternatively, two or more of the electrodes 140 and 142 may be connected to the same electrical line 144. In addition, some embodiments of the catheter device 120 may include a temperature sensor in the form of a thermocouple or thermistar 146 joined with at least one of the electrodes 142. Such a temperature sensor can be used to deliver temperature data signals to the power control system 150 (FIG. 1) during the ablation procedure (refer also to the embodiments described in connection with FIG. 12).

In some embodiments, it should be understood that the distal tip portion 130 of the catheter device may comprise a material along its outer surface that is able to deliver the negative charge along the entire tip surface (e.g. beyond the metallic surfaces of the electrodes). For example, the catheter device may comprise a polymer material that incorporates a conductive material, such as graphite (e.g., graphite nano-particles), tungsten, or a combination of graphite and tungsten, along at least the distal tip portion 130 so that the outer surface is weakly conductive compared to the metallic electrodes 140 and 142. In some circumstances, the polymer material may be formulated to be intrinsically conductive, such as polymer selected from the group consisting of polyacetylene, polypyrrole, polyaniline, polythiophene, fluorophenyl thiophene, polyphenylene vinylene, polyphenylene sulfide, polynaphthalene, and polyphenylene. As such, the continuous negative charge (described above) may pass through the weakly conductive material along the entire tip surface (not merely along the electrode surfaces) so as to reduce the likelihood of forming coagulants along a greater area of the device 120. In some embodiments, this conductive material incorporated into the catheter body may be used along the entire length of or a majority of the outer surface of the catheter body to provide the benefits described herein. It should be understood that, in other embodiments, the "negative shielding" (described in more detail below) from the metallic electrode surfaces may be sufficient to reduce the likelihood of forming coagulants along the majority of the tip portion.

Still referring to FIGS. 2-3, the distal tip portion 130 of the catheter device 120 may also include one or more irrigation ports 135. The irrigation ports 135 may be in fluid communication with a lumen network 136 extending through the elongate catheter body 125 for connection to a supply reservoir (not shown in FIGS. 2-3). Accordingly, the catheter device 120 may deliver a fluid 139 having a pH level greater than blood (e.g., a bicarbonate solution or the like) from the irrigation ports to further reduce the likelihood of forming coagulants during the ablation procedure (described in more detail below). In this embodiment, the irrigation ports 135 are disposed adjacent to the electrodes 140 and 142 so that the fluid 139 is released in the vicinity of the electrode surfaces. It is believed that fibrinogen at lower pH levels will bind more tightly to electrode surfaces. By releasing a fluid from the catheter device 120 that has a pH level higher that typical pH values for blood, the likelihood of fibrinogen binding may be reduced. For example, a bicarbonate solution having a higher pH level that blood can inhibit fibrinogen from tissue binding.

In some embodiments, the fluid 139 may also include RGD peptides of the fibrinogen molecules. The arginine lysine aspartame peptide sequence of fibrinogen is believed to be a cell recognition site for various adhesive proteins present in the extra cellular matrix and blood. For example, a peptide sequence (amino-acid residues 221-550) corresponding to Clumping Factor A (ClfA) of *Staphylococcus Aureus* can bind to the fibrinogen gamma chain C-terminus, thereby blocking fibrinogen from binding to electrode surfaces. In these circumstances, the size and orientation of the ports 135 may be selected to allow for differential circulation circumference of these two substances (e.g., bicarbonate solution and the RGD/ClfA peptides) using the same pressure infusion process. Thus, in these embodiments, the application of the negative charge along the distal tip portion 130 can be combined with the circulation of RGD/ClfA peptides and bicarbonate solution (or other high pH solution) to greatly reduce and possibly eliminate the risks of thromboembolism during RF ablation procedures. Such a technique may be used in addition to conventional heparin therapy because both mechanisms are complementary in their anticoagulant/antichar formation method.

Accordingly, the ClfA peptide sequence of *Staphylococcus Aureus* (corresponding to amino-acid residues 221-550) may be used as an anti-thrombotic agent in acute coronary syndromes like myocardial infarction, unstable angina and cerebrovascular accidents. For example, the blood coagulation factor, FXIII promotes stabilization of clot structure by catalysing the formation of covalent γ-glutamyl-ϵ-lysine peptide bonds between the fibrin γ and α chains, resulting in crosslinking between these chains altering the viscoelastic properties of the clot. This results in a stiffer clot that is also resistant to fibrinolysis. It is believed that a fibrin clot structure with thin and tightly packed fibres is associated with premature myocardial infarction. The ClfA peptide sequence of *Staphylococcus Aureus* (corresponding to amino-acid residues 221-550) may be used to reverse the effects of FXIII on fibrin clot structure to thereby create a fibrin clot structure with thicker fibres and larger pore size.

Clumping factor A (ClfA) is a surface protein of *Staphylococcus aureus* bacteria having the ability to bind the C-terminus of plasma fibrinogen gamma chain, which participates in mediating fibrinogen-platelet interaction and fibrin cross-linking, resulting in thrombus formation. It is believed that because it targets only the last 4 residues of the gamma chain of fibrinogen, ClfA is therefore more specific and the bleeding complications are expected to be less compared to that of GPIIbIIIa inhibitors.

Figure 4:
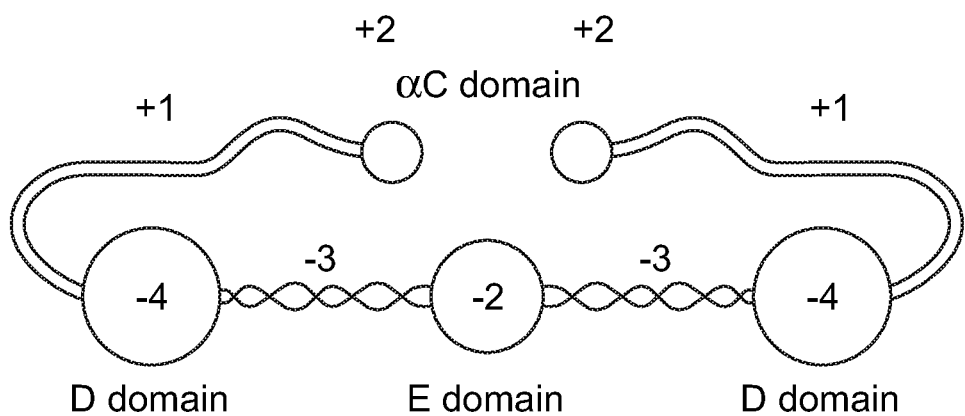
FIG. 4 is a depiction of a fibrinogen molecule.
Figure 5:
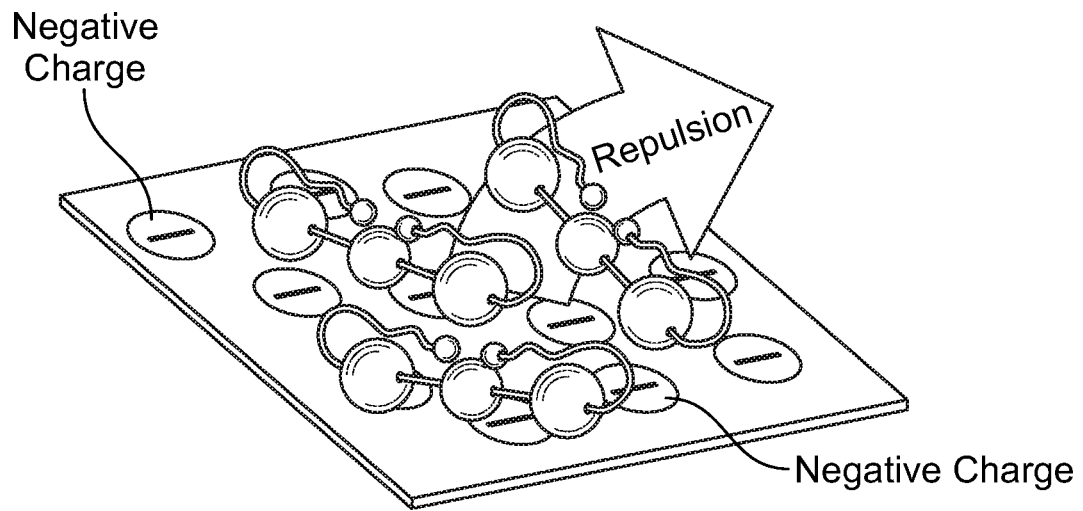
FIG. 5 is a depiction of fibrinogen molecules being repelled by a negatively charged surface.
Figure 6:
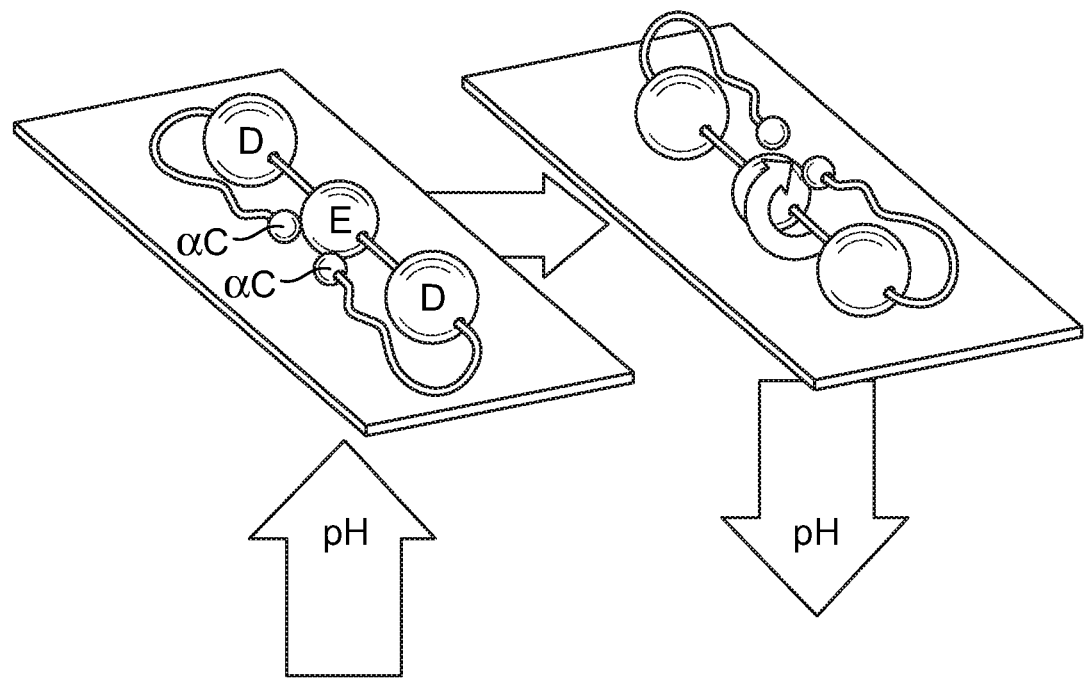
FIG. 6 is a depiction of fibrinogen molecules being biased away from a surface by circulation of a fluid having a relatively high pH level.
Figure 7:
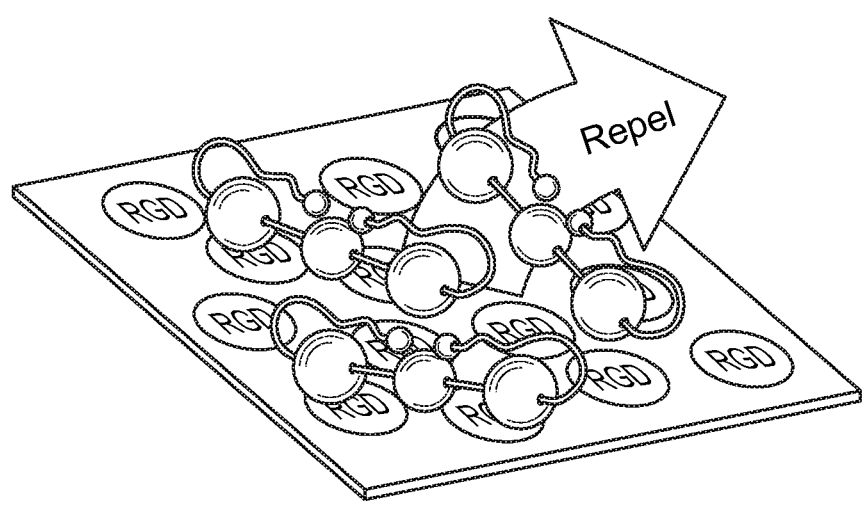
FIG. 7 is a depiction of fibrinogen molecules being repelled surface by circulation of RGD peptides of the fibrinogen molecules.

Thus, in accordance with the previously described embodiments, the catheter device 120 may employ one or more techniques to reduce the likelihood of fibrinogen bindings along the distal tip portion 130 of the elongate catheter body 125. First, the catheter device 120 may employ a negative charge that is applied along the distal tip portion (or a majority of the length of the catheter body) so as to repel the fibrinogen molecules. FIG. 4 shows a depiction of the fibrinogen molecule for illustrative purposes only. It is believed the particular sites of this molecule are associated with binding and subsequent denaturation. As illustrated in FIG. 5, when a negative charge is applied along the distal tip portion 130 of the catheter device 120, the fibrinogen molecules may be repelled or otherwise biased away from the surface, thereby reducing the likelihood of fibrinogen binding. Second, as illustrated in FIG. 6, the catheter device 120 may circulate a fluid having a pH level higher than that of the patient's blood, which may further reduce the likelihood of fibrinogen binding. Third, as illustrated in FIG. 7, the catheter device 120 may locally infuse RGD peptides along the distal tip portion 130 so as to repel fibrinogen molecules, which again may further reduce the likelihood of fibrinogen binding.

Returning now to particular examples of the power control system 150 (FIG. 1), it should be understood that there are several configurations for application of the negative charge to the catheter device 120. In one example, based on the dimensions of typical ablation catheter electrodes (4 mm to 8 mm) and the dielectric constant of blood, the capacitance at the electrode-tissue interface can be estimated to be about 1-2 µF (The applied DC voltage at the electrode-tissue interface can be maintain below about ±0.8V to avoid electrical stimulation and electrolysis at the electrode-tissue interface.) Because charge (Q)=capacitance (C)×voltage (V), the negative charge at the interface can be approximated to be about 1-2 µcoulombs. If this negative charge is delivered on a regular basis (to replenish the charge lost at the interface), the fibrinogen molecules can be effectively repelled to thereby inhibit the process of coagulation from occurring at the interface. It should be understood that the negative charge may also be deposited on the ablation tissue site, so a negative charge larger than 2 µcoulombs may be required.

Figure 8:
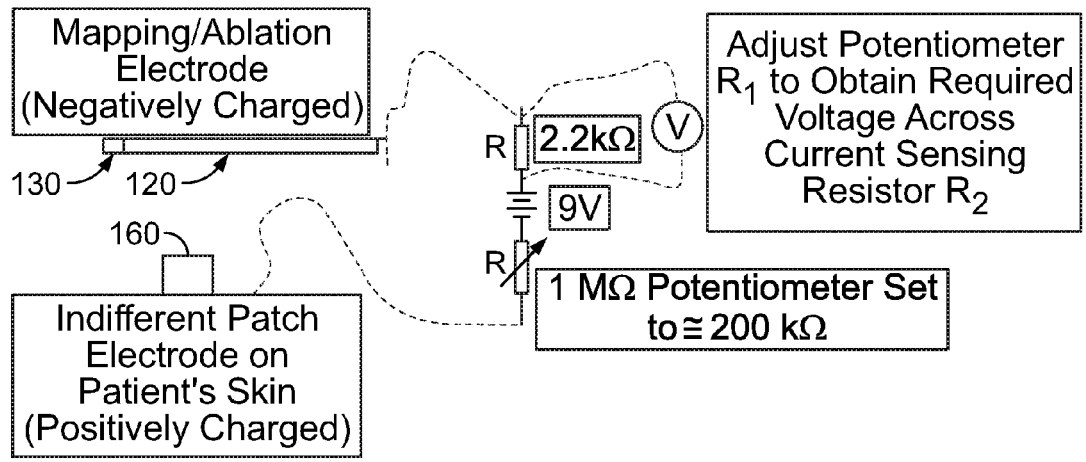
FIG. 8 is an example of configuration to deliver a negative charge to an ablation catheter device.
Figure 9:
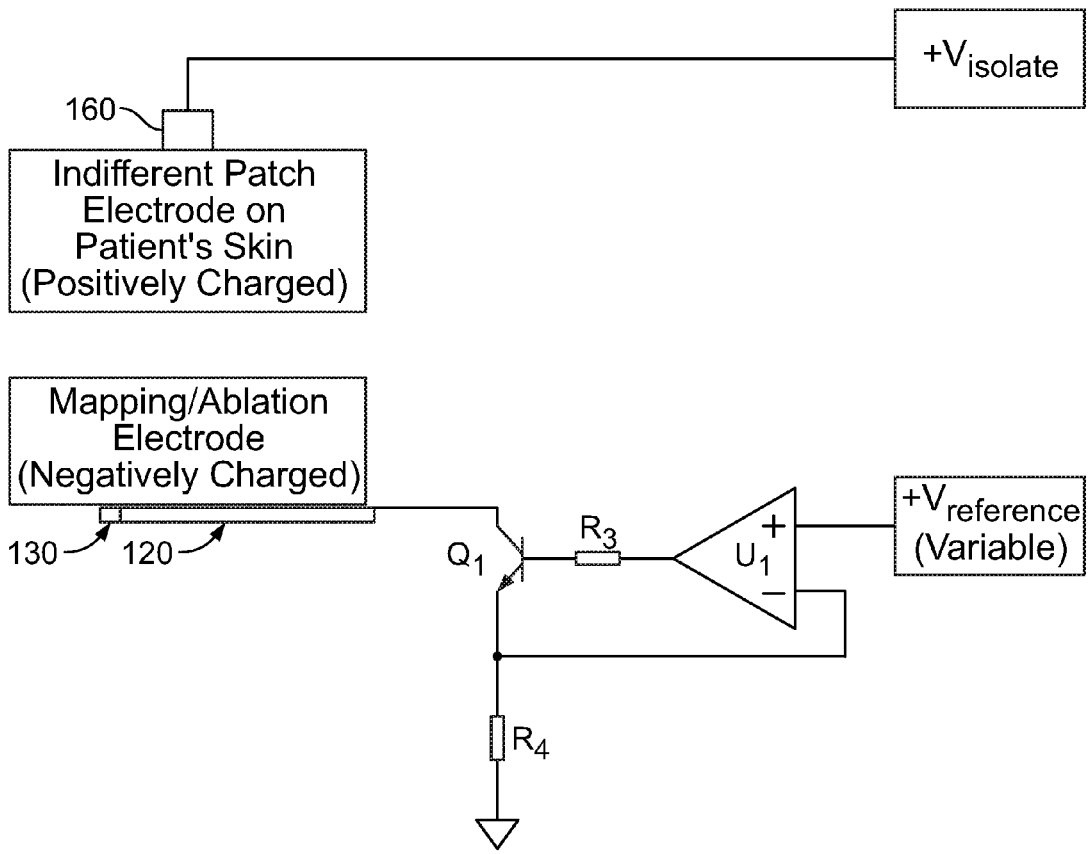
FIG. 9 is another example of configuration to deliver a negative charge to an ablation catheter device.

Referring to FIGS. 8-9, the negative charge may be delivered, intermittently or continuously, using a microprocessor-based system to measure and control charge delivery. One approach is to use a voltage source with a large resistance in series with the output that can be adjusted to produce the required current through the catheter (shown in FIG. 8). Another approach is to use a current source to deposit constant negative charge on the electrode along the distal tip portion so as to make the charge independent of the variable skin contact resistance/impedance (shown in FIG. 9). The negative charge may also be applied intermittently (e.g., using negative pulsed current). The negative charge current may be adjusted from 5 µA to 200 µA to provide the required charge to the surface, depending upon the surface area and contact capacitance. In some preferred embodiments, the negative charge current is about 50 µA (0.050 mA) to about 100 µA (0.100 mA) while the alternating current for the RF ablation is about 500 mA to about 600 mA.

It should be understood that in both example configurations shown in FIGS. 8-9, the negative charge may be delivered to a multiplicity of electrodes on the catheter by using similar parallel circuits in order to reduce or eliminate clot formation on all of them. The electrode in contact with the tissue (either during mapping or ablation) can also deposit negative charge on the surface that is being mapped and ablated, thereby reducing clot formation at the contact surface.

In those embodiments in which the negative charge is applied to multiple electrodes on a single catheter simultaneously, the catheter shaft between the metallic electrodes may accumulates less coagulum. It is believed that this is due to a "negative shielding" that occurs between the two electrodes. Such a "negative shielding" effect in the catheter shaft can be enhanced by embedding or coating the catheter body with graphite fibers, thereby creating a weakly conductive surface material between the metallic electrodes which holds onto the negative charge.

In addition or in the alternative, the negative charge deposited along the distal tip portion 130 of the catheter device 120 may be generated by forming the distal tip portion from negatively charged materials. For example, the distal tip portion 130 may incorporate a polymer material that has inherent electrostatic forces as a result of a manufacturing process. As such, the distal tip portion 130 may exhibit a low level negative charge that reduces the likelihood of fibrinogen binding, as previously described. In some circumstances, the use of the negatively charged material may be used in combination with the previously described electrical circuit that applies the negative charge to the electrodes 140 and 142 (FIG. 1) along the distal tip portion 130.

Figure 10:
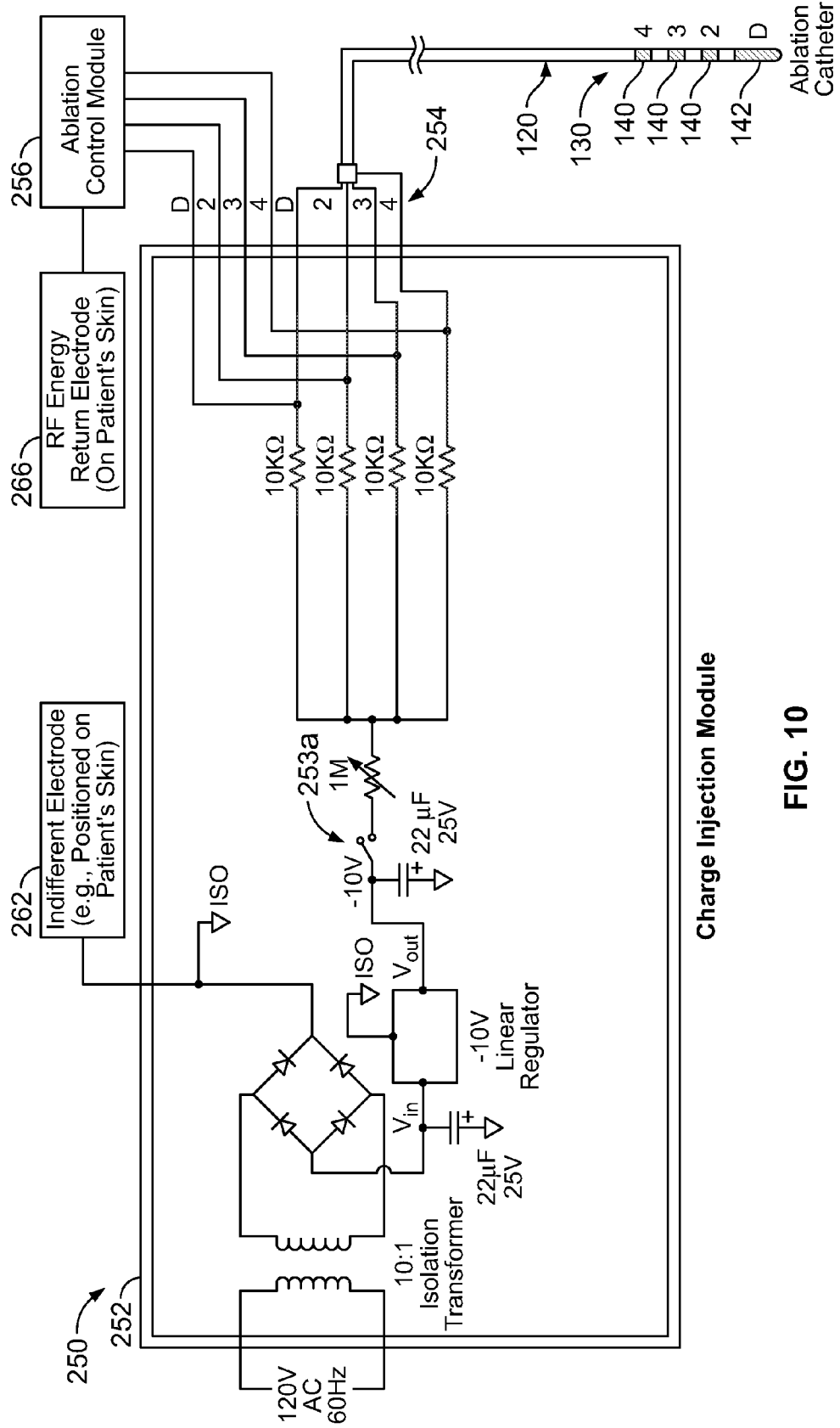
FIG. 10 is a diagram of a charge injection module for delivering a negative charge an ablation catheter device, in accordance with some embodiments.

Referring now to FIG. 10, some embodiments of a power control system 250 may include a number of modules 252 and 256 that are connectable to provide the previously described electrical output to the catheter device 120. For example, in this embodiment, the power control system 250 includes a charge injection module 252 that serves as a supplement to the ablation control module 256. In particular, the ablation control module 256 can output the RF energy through conductive lines to the ablation catheter 120 so that the RF energy is delivered from the electrodes 140 and 142 to the targeted tissue. The charge injection module 252 operates between the ablation module 256 and the ablation catheter 120 so as to deliver a negative charge bias to the ablation catheter 120. In some circumstances, the ablation control module 256 may comprise a commercially available ablation control system that may ordinarily deliver RF energy to the ablation catheter 120 without a negative charge bias. With the addition of the charge injection module 252 as shown in FIG. 10, the electrical energy delivered to the catheter 120 is supplemented with a negative charge bias that can reduce fibrinogen binding and the formation of coagulum at the interface between the distal tip portion 130 and the surround blood or bodily tissue.

Still referring to FIG. 10, the charge injection module 252 can include at least one switch device 253 that is capable of controlling the delivery of the negative charge to the catheter device 120. For example, the switch device 253 may include a toggle switch that can be actuated by a user to adjust the negative charge delivery between an "off" condition and an "on" condition. Also, in this embodiment, the charge injection module 252 include one or more outputs 254 that electrically connect the catheter device 120 with the charge injection module 252. Such outputs 254 may include one or more adapters that join electrical lines from the catheter device 120 with the charge injection module 252.

The charge injection module 252 can include a return electrode 262 that is separate from a return electrode 266 of the ablation control module 256. For example, the return electrode 266 of the ablation control module 256 may comprise an electrode patch that is placed on the patient's skin in a targeted area near the internal ablation site. As such, the RF energy delivered from the ablation control module 256 can be delivered from the distal tip potion 130 of the catheter device 120 and directed toward the RF energy return electrode 266. The return electrode 262 of the charge injection module 252 can be placed on a different region of the patient's body because it is separate from the RF energy return electrode 266. As such, the return electrode 262 of the charge injection module 252 can serve as an "indifferent" electrode on the patient's body that is not necessarily required to be placed at particular location relative to the catheter device. Instead, the return electrode 262 can include a patch electrode resting on the patient's skin that has a positive charge that equalizes the negative charge delivered to the catheter device 120 in a different portion of the patient's body.

Figure 11:
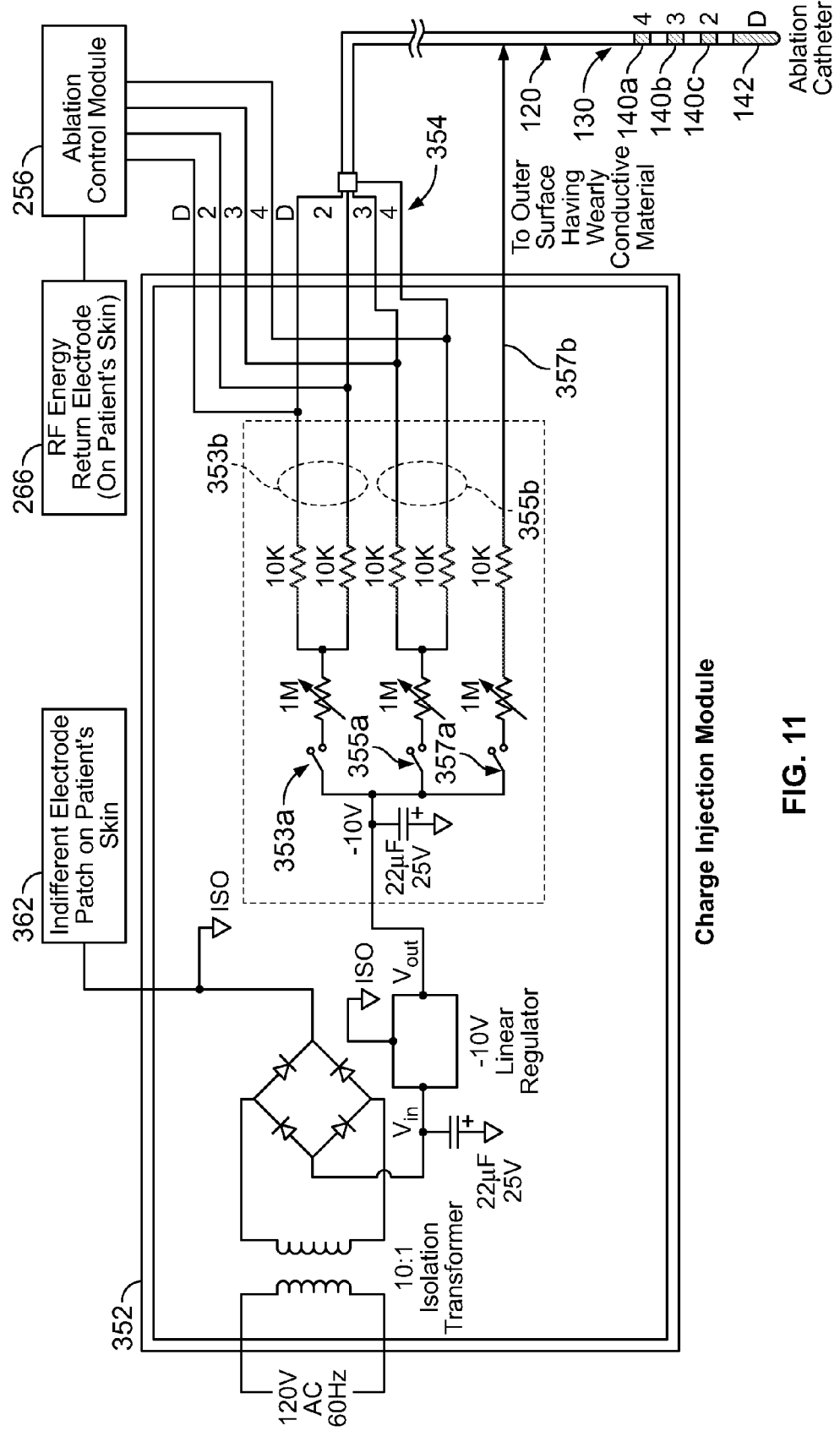
FIG. 11 is a diagram of another embodiment of a charge injection module that delivers a negative charge to various groupings of electrodes of an ablation catheter, in accordance with some embodiments.

Referring now to FIG. 11, some embodiments of a power control system 350 can be configured to independently control the negative charge that is delivered to particular groupings of electrodes 140 and 142. For example, in some embodiments, the catheter device 120 may include a plurality of electrodes 140a, 140b, 140c, and 142 arranged along the distal tip portion 130, the charge injection module 353 can be equipped to group a subset of the electrodes together for independent control the negative charge delivery to each of the electrode groups. In this embodiment, the charge injection module 352 includes a plurality of switch devices 353a, 355a, and 357a that can be independently actuated to adjust the delivery of the negative charge to particular electrode groups 353b, 355b, and 357b. For example, the switch device 353a controls the delivery of the negative charge to the group 353b consisting of electrodes 140c and 142 (i.e., the distal electrode "D" and the second electrode "2" as shown in FIG. 11). Also in this example, the switch device 355a controls the delivery of the negative charge to the group 355b consisting of electrodes 140b and 140a (i.e., the third electrode "3" and the fourth electrode "4" as shown in FIG. 11). Finally, in this example, the switch device 357a controls the delivery of the negative charge to the group 357b consisting of the weakly conductive outer surface 127 of the catheter tip portion 130 (as previously described, the catheter device 120 may comprise a polymer material that incorporates a conductive material so that the outer surface is weakly conductive compared to the metallic electrodes). Accordingly, the switch devices 353a, 355a, and 357a can be selectively operated by a user to independently control the delivery of the negative charge to the electrode groups.

As shown in FIG. 11, the charge injection module 352 depicted in FIG. 11 may serve serves as a supplement to the ablation control module 256 (as described in connection with FIG. 10). Thus, the charge injection module 352 operates between the ablation module 256 and the ablation catheter 120 so as to deliver a negative charge bias to the ablation catheter 120. Furthermore, the charge injection module 352 depicted in FIG. 11 can include one or more outputs 354 similar to those described in connection with FIG. 10. Also, the charge injection module 352 can include a return electrode 362 that is separate from the RF energy return electrode 266 of the ablation control module 256 so that the return electrode 362 can be placed on a different region of the patient's body.

Figure 12:
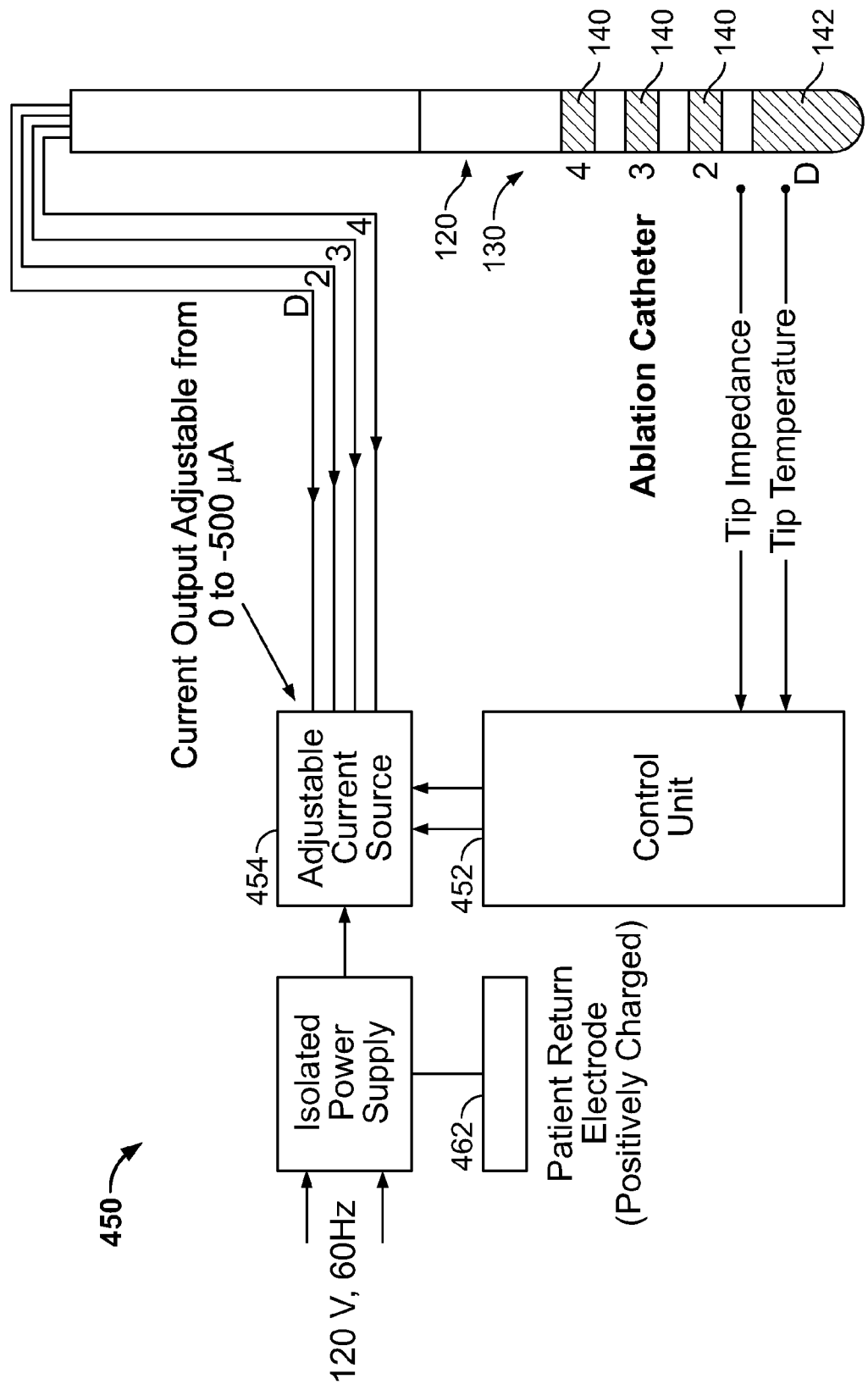
FIG. 12 a diagram of system for use in ablation therapy that provides controlled adjustment of the negative charge delivered to the ablation catheter, in accordance with some embodiments.

Referring now to FIG. 12, some embodiments of the power control system 450 can be equipped to automatically adjust the negative charge delivered to the catheter device using a microprocessor-based control loop. For example, the power control system 450 may include a microprocessor-based control unit 452 that can adjust the electrical current or negative charge that is delivered to the catheter device 120 in response to a sensed parameter (e.g., the impedance detected at the distal tip portion 130, the temperature detected at the distal tip portion 130, the amount of energy delivered to the distal tip portion 130, or the like). In this embodiment, the control unit 452 receives feedback data that is indicative of the impedance and temperature at the catheter tip. In response to this feedback data, the control unit 452 communicates with an adjustable current source 454 that is capable of providing a negative charge to the ablation catheter 120. For example, the adjustable current source 454 may be capable of adjusting the current between 0 and −500 μA so that the negative charge is delivered to the electrodes 140 and 142 of the catheter device 120. It should be understood that the catheter device 120 may also receive RF energy from an RF ablation module (as previously described) so that the RF energy is biased by the negative charge from the adjustable current source 454. Furthermore, the power control system 450 can include a return electrode 462 (e.g., a patch electrode on the patient's skin) that provides a positive charge to equalize the negative charge delivered to the catheter device 120 in a different portion of the patient's body.

In the embodiment depicted in FIG. 12, the control unit 452 can communicate with the adjustable current source to modify the electrical current or negative charge in response to the impedance or temperature at the catheter tip. For example, if the tip temperature is reduced, the control unit 452 may communicate signals that cause the current source 454 to increased the level of negative charge delivered to the catheter device 120. In another example, if the impedance at the catheter tip rises, the control unit 452 may communicate signals that cause the current source 454 to increased the level of negative charge delivered to the catheter device 120. Accordingly, as power is titrated up and there is an increase in the impedance (e.g., after an initial fall of 5 Ω or more in this embodiment), the control unit 452 can detect that an impending impedance rise from early coagulum formation is possible and will automatically cause the level of negative charge to be increases. Such an increase in the negative charge may thereby inhibit the formation of coagulum along the catheter tip portion 130.

Figure 13:
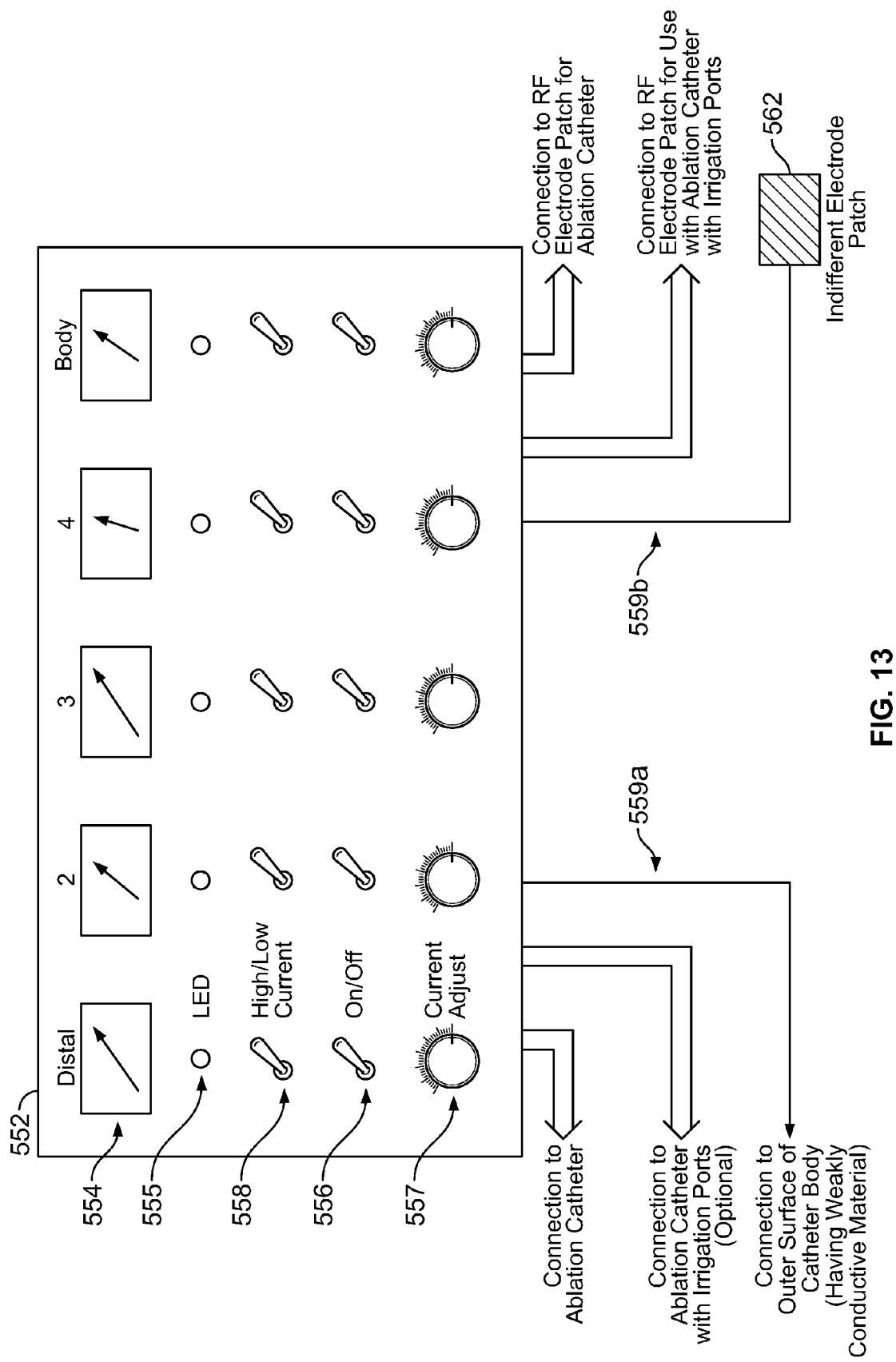
FIGS. 13-14 is a diagram of a charge injection module that delivers a negative charge to individual of electrodes of an ablation catheter, in accordance with some embodiments.
Figure 14:
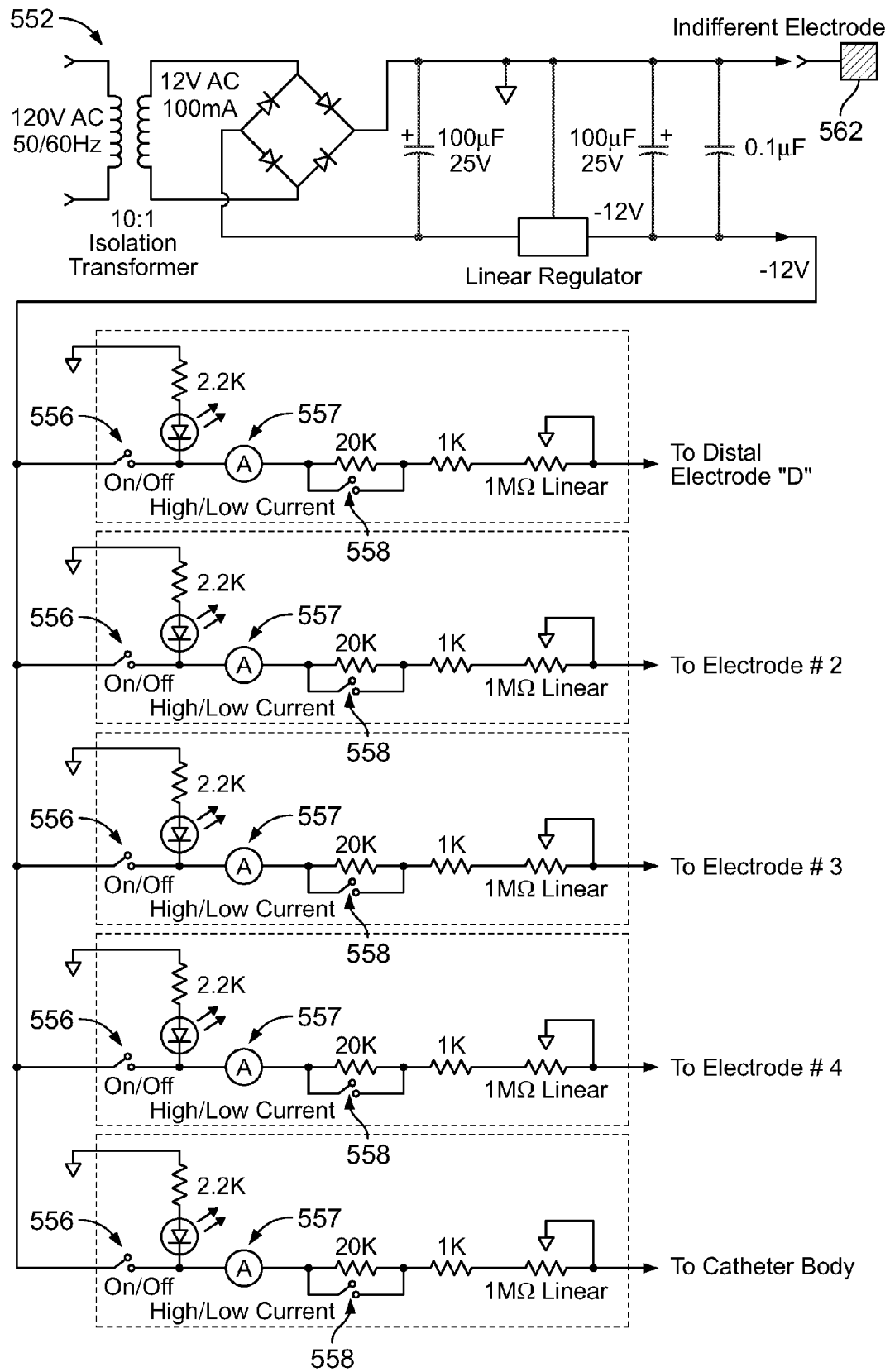

Referring now to FIGS. 13-14, some embodiments of the power control system may include a charge injection module 552 that is configured to separately control the negative charge delivery to each of the catheter electrodes (e.g., electrodes "D," "2," "3," and "4" illustrated in FIG. 10). As shown in FIG. 13, the charge injection module 252 may include a control panel that permits a user to independently control the negative charge delivery for each of the catheter electrodes. In this embodiment, the catheter electrodes include the "distal" electrode, the second electrode "2," the third electrode "3," the fourth electrode "4," and the outer surface of the catheter "body" (as indicated by the labels on the control panel depicted in FIG. 13). The control panel may include one or more display instruments 554 that indicates the level of negative charge that is currently being delivered to each of the catheter electrodes. Also, the control panel may include a power indicator LED 555 for each of the catheter electrodes. The power indicator LEDs 555 provide a quick indication to the user of which output lines are currently activated to deliver the negative charge.

The control panel of the charge injection module 552 can also include a number of switch devices 556 and 558 (FIGS. 13-14) and adjustment dials 557 (FIGS. 13-14) that permit the user to independently control each of the output lines to the catheter electrodes. In this embodiment, the control panel includes a toggle switch 556 for each of the catheter electrodes. Each toggle switch 556 is configured to adjust the negative charge delivery between an "off" condition and an "on" condition. As such, the user may activate some of the toggle switches 556 to deliver a negative charge to some of the catheter electrodes while the remaining toggle switches 556 are in the "off" condition so that the corresponding catheter electrodes do not receive the negative charge. Also in this embodiment, the control panel includes a charge level adjustment dial 557 for each of the catheter electrodes. Each of the charge level adjustment dials 557 can be actuated by the user to increase or decrease the level of current or negative charge that is delivered to the corresponding catheter electrode. Finally, in this embodiment, the control panel includes a high/low current switch 558 for each of the catheter electrodes. The high low current switch 558 permits the user to adjust the electrical current output range, which affects the range of negative charge levels that can be delivered to the corresponding catheter electrode. For example, when the high/low current switch 558 is arranged in the "low" position, the electrical output range can be between 0 µA and −500 µA. When the high/low current switch 558 is arranged in the "high" position, the electrical output range is increased to a range between −500 µA and −10 mA. As such, the user can make adjustments to the negative charge at a fine resolution (e.g., 10 µA) when the high/low current switch 558 is arranged in the "low" position, and at a different resolution (e.g., 50 µA) when the high/low current switch 558 is arranged in the "high" position.

As shown in FIG. 13, the charge injection module 552 can include negative outputs 559$a$ and positive outputs 559$b$. For example, in this embodiment, the negative outputs 559$a$ are connectable to electrode lines of one or more types of ablation catheters to deliver a negative charge bias to catheter electrodes (e.g., along with the RF ablation energy). Also, the negative outputs 559$a$ may include a port that is connectable with a line to the outer surface of the ablation catheter body (e.g., to the weakly conductive surface along the distal tip portion). The positive outputs 559$b$ may be used to connect with RF energy return electrodes that are arranged on the patient's skin to direct the RF ablation energy from the catheter tip. Furthermore, the positive outputs 559$b$ may include a port that is connectable with a return electrode 562 (e.g., a patch electrode on the patient's skin) that provides a positive charge to equalize the negative charge delivered from the charge injection module 552 to the catheter device.

It should be understood from the description herein that these concepts can be applied to other catheter devices or implantable devices that come into contact with blood so as to reduce the formation of coagulum. In a first example, an angiographic catheter device may be constructed with a surface that can be negatively charged during use. In these circumstances, the entire length of the outer surface of the angiographic catheter device may exhibit a negative charge to reduce the likelihood of clot formation along the whole catheter body. Such a negative charge on the angiographic catheter may reduce the likelihood of clot formation during angiography and may reduce the usage of heparin or other anticoagulant drugs during the procedure.

In second example, a vascular sheath device used to deliver intravenous medications into the central venous system could also have a negatively-charged conductive coating, with very small sources of power delivering a negative charge on a continuous or intermittent basis. For instance, a Hickman catheter may be equipped with a conductive coating along an outer surface so as to provide a negative charge on a continuous or intermittent basis. As such, the negatively-charged Hickman catheter can be used to deliver medication or other treatment while the negatively-charged outer coating reduces the likelihood of coagulum formation. Alternatively, a trans-septal sheath may be equipped with a conductive coating along an outer surface so as to provide a negative charge on a continuous or intermittent basis. The negatively-charged trans-septal sheath can be delivered to the heart as a pathway for an ablation catheter (from the right atrium to the left atrium) while the negatively-charged outer coating reduces the likelihood of coagulum formation.

In a third example, a hemodialysis system may incorporate an electrically charged system that applies a negative charge to some or all of the catheters, tubes, and reservoirs of the dialysis machine pumps that contact the blood so as to reduce the need for heparin and reduce thrombosis.

In a fourth example, a power control system can deliver a negative charge to a portion of a cardiac instrument that applies RF energy or heat energy during a cardiac procedure, such as a wire, mesh, tube, stent, blade, or other elements. Such a negative charge on a conductive portion of the cardiac instrument may reduce the likelihood of clot formation during the cardiac procedure and may reduce the usage of heparin or other anticoagulant drugs during the procedure. In some embodiments, the negative charge can be delivered to the RF ablation elements that are used to close or "weld" bodily tissue (e.g., to close a patent foramen ovale). These embodiments may employ a power control system can deliver a negative charge to the wires, stents, and other cardiac instruments, such as the instruments described in PCT Publication No. WO2007/038609 and U.S. Pat. Publication No. 2007/0093805 (both of which are incorporated herein by reference). As previously described, the power control system can be configured to deliver the negative charge to the instrument-blood interface (especially to the portions of the instrument in the left atrium during operation) so as to reduce the formation of coagulum. It should be understood from the description herein that these embodiments may be modified to include a return electrode (e.g., an indifferent electrode in contact with some portion of the patient's body) that provides a positive charge that equalizes the negative charge being applied to the instrument-blood interface. In other embodiments, the negative charge can be delivered to RF heat cautery or cutting elements that are used for percutaneous valve removal or repair. As such, a power control system can deliver a negative charge to the conductive surfaces or the cautery or cutting elements, such as the instruments described in U.S. Pat. Publication Nos. 2006/0229659, 2005/0075724, and 2003/0216764 (all of which are incorporated herein by reference). Again, such embodiments may be modified to operate in conjunction with a return electrode (e.g., an indifferent electrode in contact with some portion of the patient's body) that provides a positive charge that equalizes the negative charge being applied to the instrument-blood interface.

Likewise, in a cardiac procedure, the power control system and the ablation catheter embodiments may be employed to provide non-thermal ablation of cardiac tissue. In particular, the ablation catheter device 120 and the power control system 150 can be configured to deliver ablative energy to tissue without resulting in the substantially elevated temperatures associated with RF ablation. For instance, the ablation catheter device 120 can provide low-energy DC ablation at selected cardiac tissue (e.g., at the triangle of Kock) for the treatment of resistant atrial flutter. In such circumstances, the ablation catheter device 120 may deliver low-energy DC power in shocks of about 2 to about 40 J to the targeted tissue. Similar to previously described embodiments, the ablation catheter device 120 can be equipped with one or more sensors proximate the distal tip to determine how much ablation is occurring during the DC-nonthermal ablation process. In this non-thermal ablation embodiment, the sensors may not necessarily include a temperature senor, but instead may include one or more pH sensors arranged near the electrodes. The pH sensor can be employed to detect hydrogen gas in the bubbles that form near the electrode-tissue interface. Also, the sensors for the non-thermal ablation catheter device may include one or more impedance sensors. In some cases, the DC ablation electrodes can also serve as the impedance sensors to determine changes in impedance near the electrode-tissue interface. The ablation catheter device 120 can be equipped with an impedance sensor or electrogram threshold sensor along the distal tip portion to provide feedback indicative of tissue contact. In order to determine that there is tissue contact during the DC-nonthermal ablation process, a differential impedance sensor (e.g., two sensor electrodes wherein one is arranged more proximally on the distal electrode or on the proximal electrode itself), can be employed to indicate a change in the impedance within a particular range (e.g., typically 5-10 Ohm decrease) to allow continued delivery of the DC energy. A second option (to determine that there is tissue contact during the DC-nonthermal ablation process), can include an electrogram threshold sensor along the distal tip of the ablation catheter device 120 automated electrogram so as to automatically detect a decrease or other change (e.g., fragmentation, duration increase, or the like) as feedback indicative of tissue contact and ablation of the underlying tissue. In addition or in the alternative, the ablation catheter device 120 may include one or more flow velocity sensors to provide feedback regarding the flow of blood around the distal tip of the ablation instrument. It should be understood from the description herein that, in some embodiments, the ablation catheter device 120 and the power control system 150 can be configured to combine RF and DC energy capabilities so as to contemporaneously deliver both RF ablation energy and DC ablation energy during the same procedure or to separately deliver RF ablation energy and DC ablation energy using the same catheter device 120.

Figure 15:
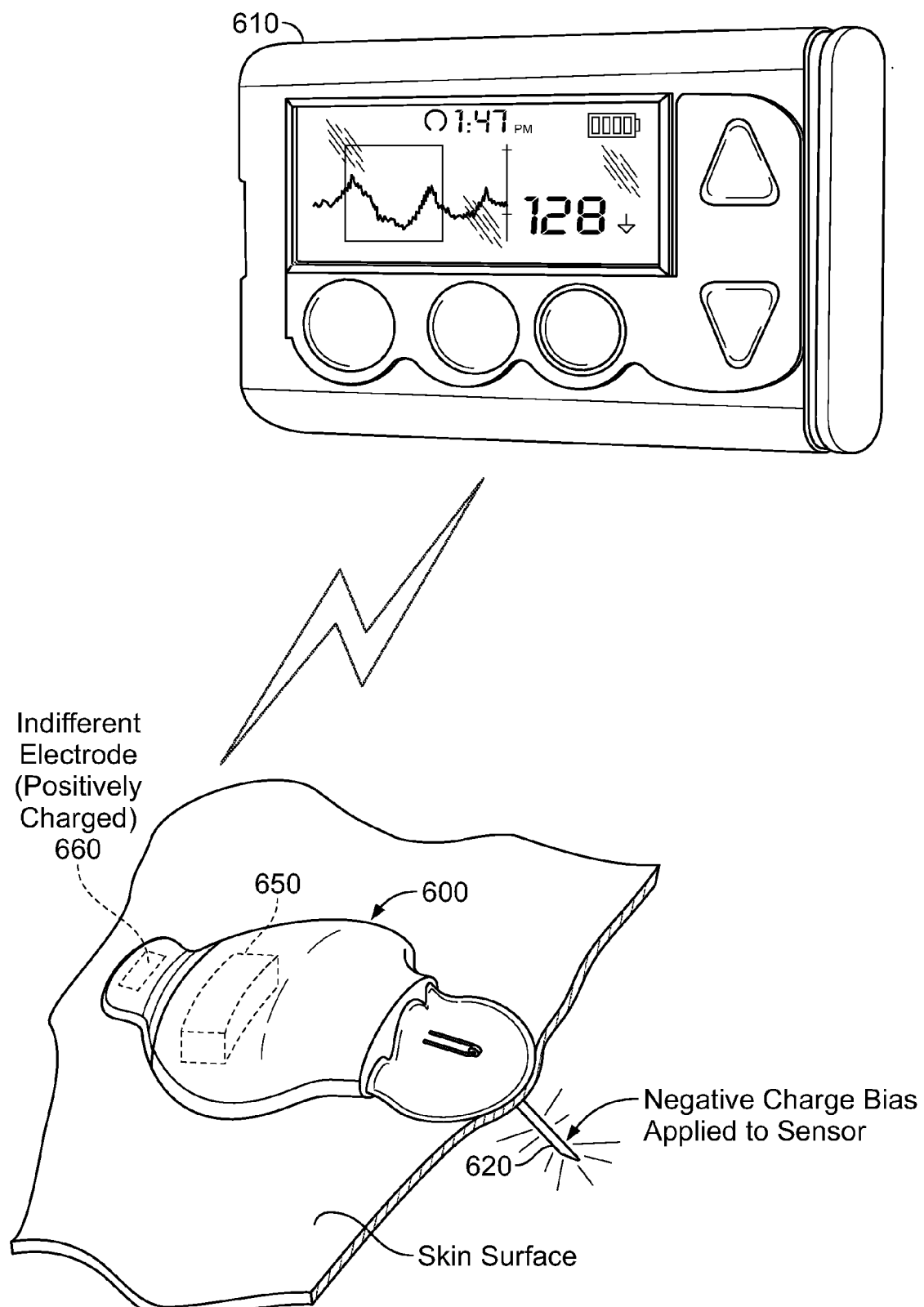
FIG. 15 is a perspective view of a blood glucose sensor system that delivers a negative charge to a conductive surface of an implantable glucose sensor so as to inhibit the formation of coagulum, in accordance with some embodiments.

Referring now to FIG. 15, in a fifth example, a power control system can deliver a negative charge to a conductive surface of an implantable glucose sensor 600 so as to inhibit the formation of coagulum on the implanted sensor shaft 620 that would otherwise reduce the sensor accuracy and service life. As shown in FIG. 15, the glucose sensor 600 may comprise a sensor shaft 620 that penetrates under the skin (e.g., into the subcutaneous layer) while the sensor housing is adhered to the skin. The sensor housing may contain a power source and a communication circuit (not shown in FIG. 15) that permits the sensor data to be wireless transmitted to controller device 610. The controller device 610 can include a display to communicate the sensed glucose level and one or more buttons for user interaction. In this embodiment, the sensor also includes the power control system 650 that delivers a negative charge to the implanted sensor shaft 620 to thereby inhibit the formation of coagulum. In particular embodiments, the power control system 650 may operate in a manner similar to the charge injection module (described in connection with FIG. 10) in that it supplements the sensor shaft 620 with a negative charge bias. The power control system 650 is also connected to a return electrode 660 that contacts the user's skin when the sensor is adhered to the skin. As such, the return electrode 660 may provide a positive charge that equalizes the negative charge being applied to the sensor shaft 620.

The level of the negative charge applied to the sensor shaft 620 can be selected so as to inhibit the formation of coagulum while not substantially affecting the accuracy of the glucose sensor 600. Accordingly, the application of the negative charge to the implanted sensor shaft 620 may reduce the formation of coagulum on the sensor shaft 620, which would otherwise deposit on the sensor shaft 620 (e.g., due to a foreign body reaction) and shorten the useful life of the sensor 600. For example, the glucose sensor 600 that is equipped to deliver the negative charge to the implanted portion 620 may have a useful life of about 7 days or more, about 7 days to about 14 days, and in some embodiments about 7 days to about 10 days.

The embodiments of a glucose sensor having a power control system to deliver a negative charge to the implanted sensor portion are not limited to the example depicted in FIG. 15. For example, the glucose sensor may have other features—in addition to the application of the negative charge (described above)—that reducing biofouling such as those described in U.S. Pat. No. 7,153,265 to Vachon (incorporated herein by reference). Furthermore, the glucose sensor may have other configurations and sizes such as those described in U.S. Pat. No. 5,569,186 to Lord et al. (incorporated herein by reference). It should be understood from the description herein that these sensor configurations may be modified to contain or otherwise operate in conjunction with a return electrode (e.g., an indifferent electrode in contact with some portion of the patient's body) that provides a positive charge that equalizes the negative charge being applied to the implanted sensor shaft.

Figure 16:
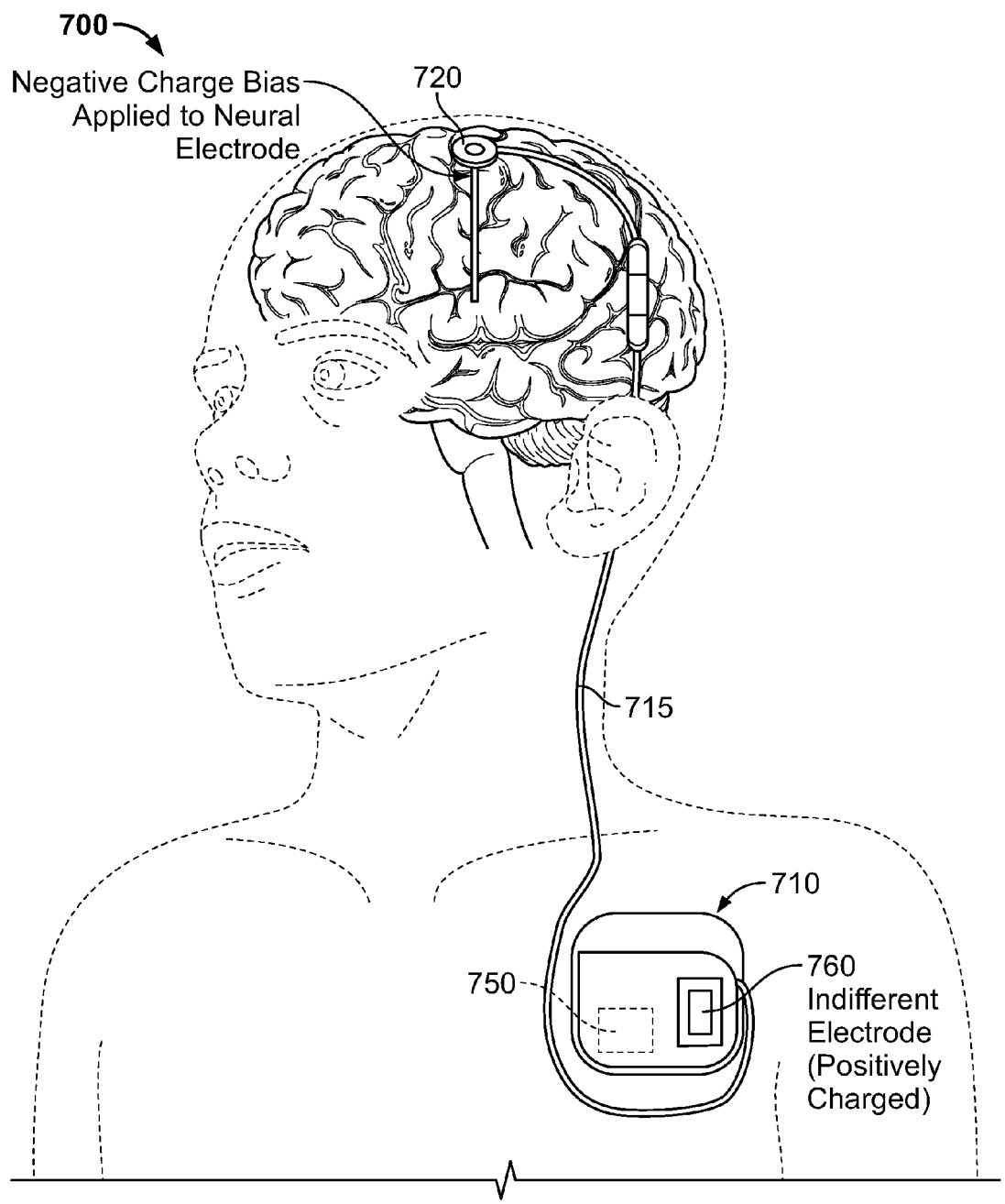
FIG. 16 is a perspective view of brain treatment instrumentation that applies a negative charge to indwelling neural electrodes or the like so as to inhibit the formation of coagulum, in accordance with some embodiments.

Referring now to FIG. 16, in a sixth example, brain treatment instrumentation (e.g., deep-brain stimulation electrodes, cortical mapping electrodes, sensing electrodes for detection of epileptic events, peripheral nerve stimulators to treat pain, and others) may incorporate a power control system that applies a negative charge to indwelling neural electrodes or the like so as to inhibit the formation of coagulum. In this embodiment, the brain treatment instrumentation 700 includes a neural electrode 720 that is implanted in the brain to serve as a deep-brain stimulation electrode. A neurostimulator device 710 may be implanted in the patient's body (e.g., proximate the clavicle) so that electrical stimulation signals can be delivered to the neural electrode 720 via an electrical lead 715. As such, the neural electrode 720 can be used to deliver deep-brain stimulation to a targeted region of the brain. A power control system 750 may be arranged in the neurostimulator device 710 so as to deliver a negative charge to the implanted neural electrode 720. As previously described, such a negative charge applied to the implanted electrode 720 may reduce the likelihood of coagulum formation on or near the electrode body. In certain embodiments, the power control system 750 may operate in a manner similar to the charge injection module (described in connection with FIG. 10) in that it supplements the implanted electrode 720 with a negative charge bias. The power control system 750 is also connected to a return electrode 760 that contacts the user's body. For example, the return electrode 760 may be arranged on an outer surface of the neurostimulator device 710 so that the return electrode 760 abuts with the underside of the patient's skin or with other bodily tissue. As such, the return electrode 760 may provide a positive charge that equalizes the negative charge being applied to the neural electrode 720.

The level of the negative charge applied to the neural electrode 720 can be selected so as to inhibit the formation of coagulum while not substantially affecting the delivery of the stimulation energy. Accordingly, the application of the negative charge to the neural electrode 720 may reduce the formation of coagulum while the neurostimulator device 710 continues to deliver the deep-brain stimulation energy to the targeted region of the brain.

The embodiments of brain treatment instrumentation having a power control system to deliver a negative charge to one or more neural electrodes are not limited to the deep-brain stimulation example depicted in FIG. 16. For example, the brain treatment instrumentation may include neural electrodes with other configurations and treatment purposes, such as the instrumentation described in U.S. Pat. Publication Nos. 2007/0016094 and 2006/0206166 and in PCT Publication No. WO07/079181 (all of which are incorporated herein by reference). It should be understood from the description herein that these brain treatment systems may be modified to contain or otherwise operate in conjunction with a return electrode (e.g., an indifferent electrode in contact with some portion of the patient's body) that provides a positive charge to equalize the negative charge being applied to the implanted sensor shaft.

Finally, it should be understood from the description herein that the reverse approach (e.g., positively charging a surface to induce rapid clot formation) may also be employed on any number of medical devices. For example, as an alternative to alcohol ablation of the septum in hypertrophic cardiomyopathy (where one does not have total control of the alcohol flow), a thin wire device could be placed in the required artery to be ablated and charged positively after correct placement to induce rapid clot formation, with consequent interruption of blood flow. In another example, as a means of anchoring unstable catheters or wires (e.g., a pacemaker lead) immediately after placement, a positive charge on the delivery catheter surface or lead surface could be used to induce clot and thereby cause the catheter to adhere to the vessel wall temporarily while fibrosis is taking place, reducing the likelihood of lead dislodgement. In a further example, superficial bleeding could be reduced by using conductive adhesive patches that could be positively charged to enhance clot formation and hemostasis.

Experimental Data

Experiments were conducted using ablation catheter devices mounted to dissected tissue of a pig heart (left ventricle wall tissue) and using ablation catheter devices suspended in heparinized pig blood. Some of the electrodes on the ablation catheter devices were provided with a negative charge, some were provided with no charge, and some were provided with a positive charge. After a timed "burn," a comparison of the microscopic coagulum/fibrinogen formation was performed. In these experiments, a small adapter was built for an EPT ablation box with a source of DC voltage and a variable current-limiting resistor in series with the output of the EPT system.

Figure 17:
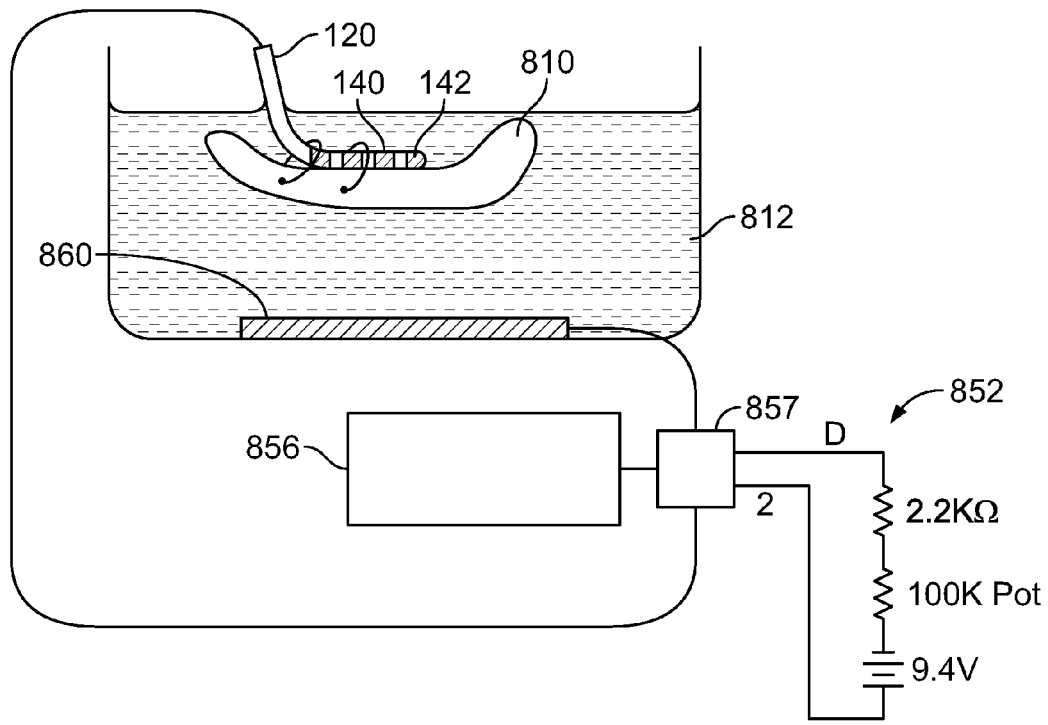
FIGS. 17-18 are models of setups used in test experiments.

For example, as shown in FIG. 17, an adapter 852 designed to provide the desired DC offset was connected with an EPT ablation unit 856 via a personality module 857 (commercially available from EP Technologies/Boston Scientific). The ablation catheter 120 was connected to the circuit so that the electrodes 140 and 142 of the ablation catheter 120 exhibited a negative charge bias during the RF ablation procedure. The ablation catheter 120 was sutured to the dissected pig heart tissue 810, which was immersed in approximately 750 ml of heparinized pig blood 812. The return electrode 860 was also immersed in the heparinized pig blood 812. After the ablation experiment, the electrodes 140 and 142 on the ablation catheter 120 were visually inspected. The preliminary results showed that the negatively charged area did not exhibit any visible coagulum (e.g., clots) and that the positively charged area (on the return electrode) exhibited significant visible coagulum (e.g., clot).

Figure 18:
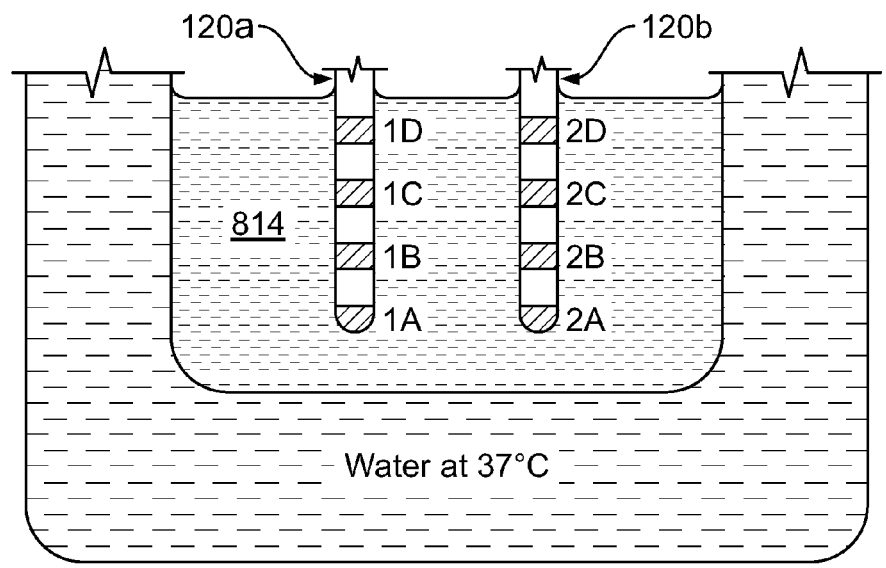
Figure 19A:
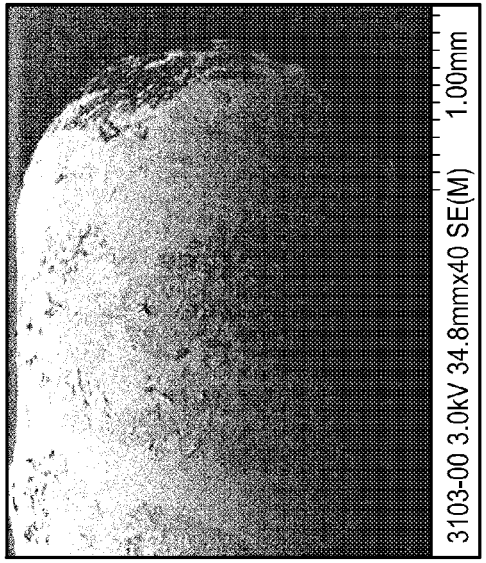
FIGS. 19A-23D are magnified images of electrode surfaces that were exposed to blood during particular experiments.
Figure 20A:
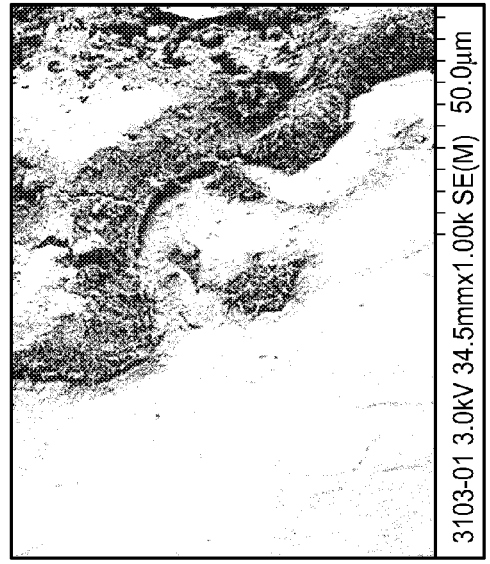
Figure 19B:
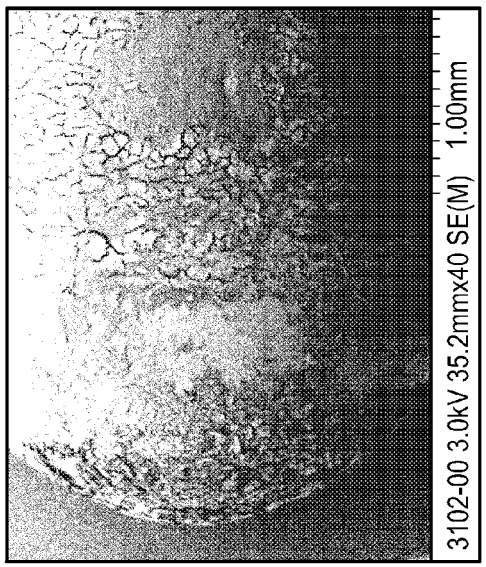
Figure 20B:
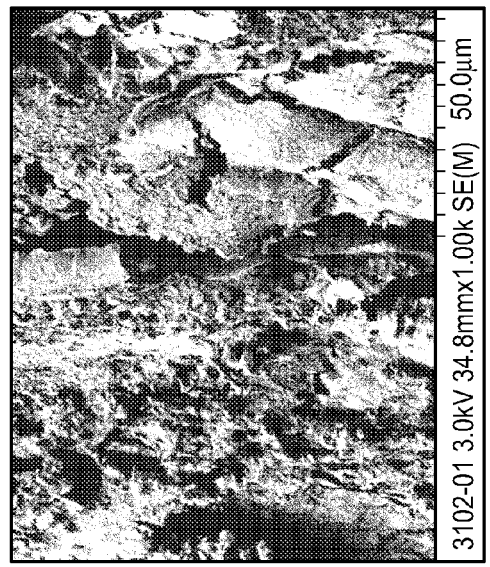
Figure 22A:
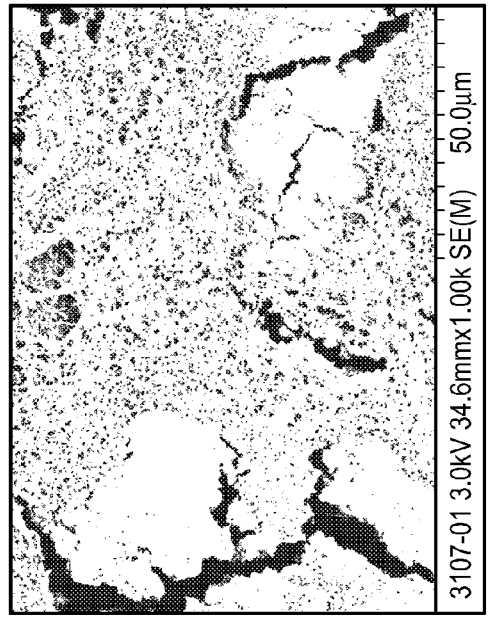
Figure 22B:
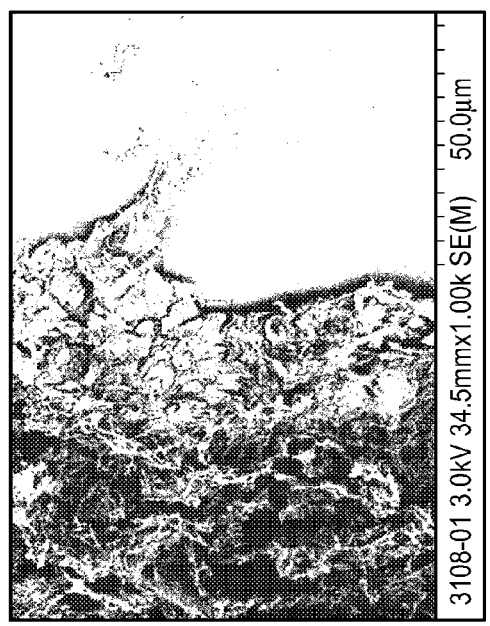
Figure 21A:
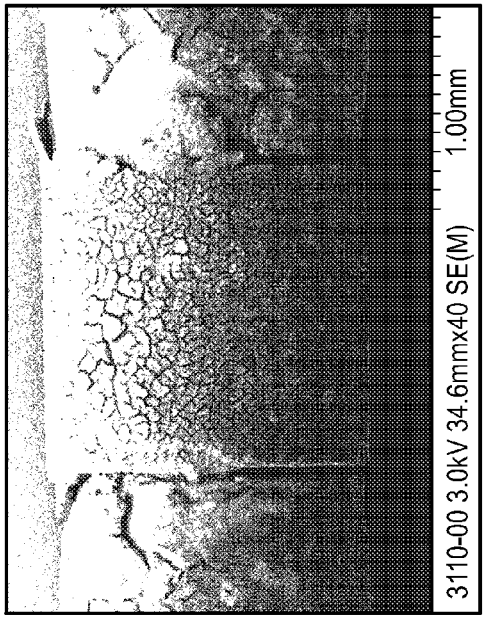
Figure 21B:
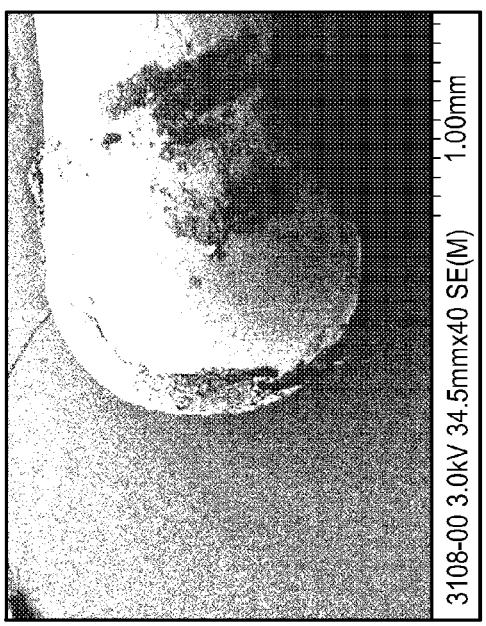
Figure 23A:
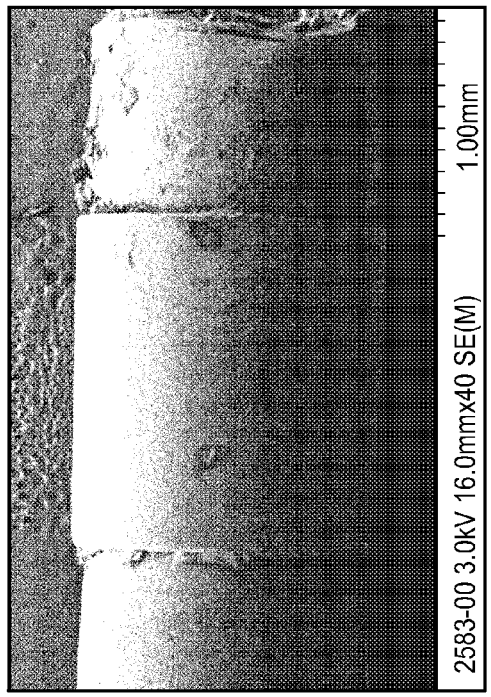
Figure 23C:
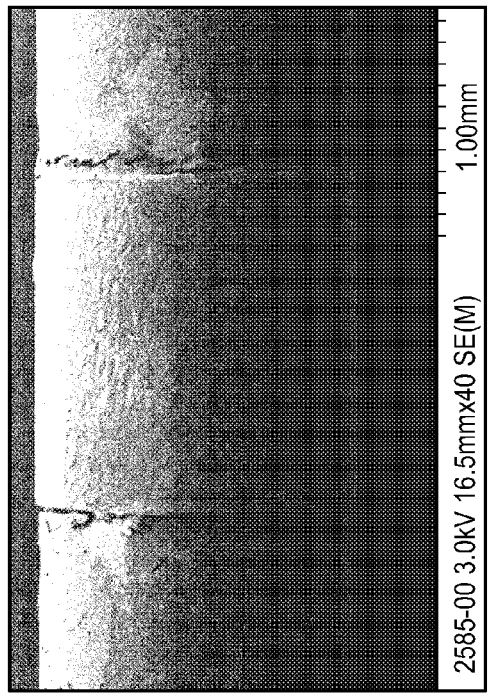
Figure 23B:
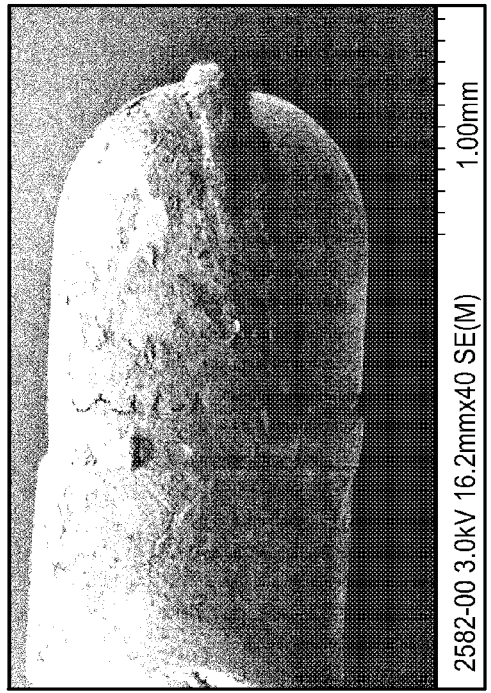
Figure 23D:
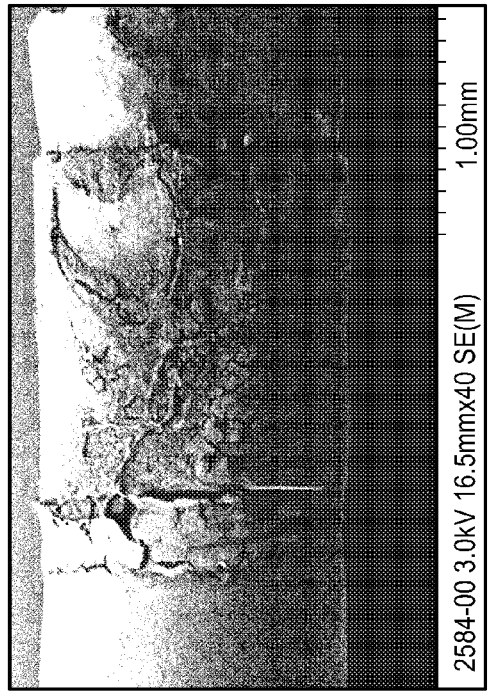

In another example, as shown in FIG. 18, ablation catheters 120a and 120b were suspended in a pool of heparinized pig blood 814. Some of the electrodes on the ablation catheter devices 120a-b were provided with a negative charge, some were provided with no charge, and some were provided with a positive charge. The electrodes were immersed in the pig blood 814 for approximately 30 minutes. At the end of 30 minutes, the electrodes along the ablation catheters tips were inspected visually. The preliminary results showed that the negatively charged area did not exhibit any visible coagulum (e.g., clots) and that the positively charged area (on the return electrode) exhibited some visible coagulum (e.g., clot).

The electrodes along the ablation catheters tips were then cut and deposited into four separate containers and then sent for electron microscopy processing and imaging. The electron microscope images for the experiments in pig blood 814 are shown in FIGS. 19A-22B. Comparing FIGS. 19A-B to FIGS. 20A-B, the electrode surfaces that were negatively charged during the ablation procedure in pig blood 814 exhibited significantly less coagulum/fibrinogen formation. Also, as shown in FIGS. 21A-B and FIGS. 22A-B, the electrode surfaces that were negatively charged during exposure to the pig blood 814 (without an ablation procedure) exhibited significantly less coagulum/fibrinogen formation.

Finally, similar experiments were carried out using canine blood (not shown), in which some electrode surfaces were negatively charges, some were positively charged, and some were uncharged. As shown in FIGS. 23A-D, the electrode surfaces that were negatively charged during the exposure to canine blood exhibited less coagulum/fibrinogen formation.

A number of embodiments of the invention have been described. Nevertheless, it will be understood that various modifications may be made without departing from the spirit and scope of the invention. Accordingly, other embodiments are within the scope of the following claims.

What is claimed is:

1. A system, comprising:
   an elongate catheter body having one or more electrodes exposed along a distal portion of the catheter body and configured to be directed to a targeted tissue site;
   means for controlling delivery of ablation energy and a negative charge to the electrodes along the distal portion of the catheter body in a manner that both delivers the ablation energy to the electrodes while the distal portion is directed to the targeted tissue site and delivers the negative charge to the electrodes so as to repel fibrinogen molecules away from the electrodes, the negative charge delivered to the electrodes being different from and a supplement to the ablation energy.

2. The system of claim 1, wherein the elongate catheter body further comprises at least one irrigation port along the distal portion configured to output a fluid having a pH level greater than human blood.

3. The system of claim 2, further comprising a source containing the fluid which comprises a bicarbonate solution.

4. The system of claim 2, further comprising a source containing the fluid which includes RGD peptides of fibrinogen molecules.

5. The system of claim 1, wherein said means for controlling includes a charge injection module that delivers the negative charge to the electrodes and includes an ablation control module that outputs the ablation energy to the electrodes.

6. The system of claim 5, wherein the charge injection module operates between the ablation control module and the electrodes of the catheter so as to deliver the negative charge bias as the supplement to the ablation energy from the ablation control module.

7. The system of claim 5, wherein the ablation control module of said means for controlling is configured to deliver RF ablation energy to electrodes exposed along the distal portion.

8. The system of claim 7, wherein the RF ablation energy includes an electrical signal characterized by an AC waveform without a DC offset so that the electrical charge of the ablation energy is neutral for each cycle.

9. The system of claim 8, wherein the negative charge delivered to the electrodes comprises a continuous electrical current that adds a DC offset to the AC waveform so that a negative charge bias is delivered to the electrodes.

10. The system of claim 9, wherein the negative charge serves as the supplement to the ablation energy so as to produce a composite waveform characterized by 50 Vrms with a 0.2V DC voltage offset.

11. The system of claim 9, wherein the negative charge serves as the supplement to the ablation energy so as to produce a composite waveform characterized by 600 mA rms with a continuous current offset of about 50 μA (0.050 mA) to about 100 μA (0.100 mA).

12. The system of claim 5, wherein the charge injection module includes an indifferent return electrode configured to provide a positive charge to equalize the negative charge delivered to the one or more electrodes at the distal portion of the catheter body.

13. The system of claim 12, wherein the ablation control module includes an RF energy return electrode positioned separately from the indifferent return electrode.

14. The system of claim 1, wherein said means for controlling is configured to deliver the negative charge to the electrodes as an electrical current magnitude that is below a muscle tissue stimulation threshold for the targeted tissue site.

15. The system of claim 1, wherein at least part of the distal portion of the catheter body comprises a polymer material that incorporates a conductive material so that a continuous negative charge is delivered to an outer surface of the catheter body from said means for controlling.

16. The system of claim 15, wherein said at least part of the distal portion of the catheter body comprises the polymer material that incorporates the conductive material selected from the group consisting of graphite, tungsten, and a combination of graphite and tungsten.

17. The system of claim 1, wherein said means for controlling is configured to deliver the negative charge intermittently to the one or more electrodes.

18. The system of claim 1, further comprising one or more sensors that are positioned at the distal portion of the catheter body and that are configured to receive one or more sensor data signals, wherein said means for controlling comprises a microprocessor-based unit that controls the delivery of the negative charge by adjusting the output of the negative charge in response to said one or more sensor data signals.

19. The system of claim 18, wherein the one or more sensors at the distal portion of the catheter body comprises a temperature sensor to detect the temperature at the distal portion of the catheter body.

20. The system of claim 18, wherein the one or more sensors at the distal portion of the catheter body comprises an impedance sensor to detect the electrical impedance at the distal portion of the catheter body.

* * * * *